US008605964B2

(12) United States Patent
Fichtinger et al.

(10) Patent No.: US 8,605,964 B2
(45) Date of Patent: Dec. 10, 2013

(54) MARKER LOCALIZATION USING INTENSITY-BASED REGISTRATION OF IMAGING MODALITIES

(75) Inventors: Gabor Fichtinger, Kingston (CA); Purang Abolmaesumi, Vancouver (CA); Zahra Karimaghaloo, Montreal (CA); Pascal Fallavollita, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 619 days.

(21) Appl. No.: 12/709,195

(22) Filed: Feb. 19, 2010

(65) Prior Publication Data
US 2010/0239144 A1    Sep. 23, 2010

Related U.S. Application Data

(60) Provisional application No. 61/202,354, filed on Feb. 20, 2009.

(51) Int. Cl.
*G06K 9/00*    (2006.01)

(52) U.S. Cl.
USPC .......................................... 382/128; 382/261

(58) Field of Classification Search
USPC .......................................... 382/128, 261, 190
See application file for complete search history.

(56) References Cited

U.S. PATENT DOCUMENTS

2005/0213841 A1* 9/2005 Linguraru et al. ............ 382/261

OTHER PUBLICATIONS

Karimaghallo, Z. et al., "Intra-operative localization of brachytherapy implants using intensity-based registration" 7th imaging Symposium of the Imaging Network of Ontario, poster (2008).*
Hummel, J., et al., "2D/3D registration of endoscopic ultrasound to CT volume data": Physics in Medicine and Biology, vol. 53, 4303-4316 (2008).
Penney, G.P., et at., "Cadaver validation of intensity-based ultrasound to CT registration" Medical Image Analysis, vol. 10, 385-395 (2006).
Wein, W., et al., "Automatic CT-ultrasound registration for diagnostic imaging and image-guided intervention," Medical Image Analysis, vol. 12, 577-585 (2008).
Karimaghaloo, Z.,. et al., "Intra-operative localization of brachytherapy implants using intensity-based registration" SPIE Medical Imaging, vol. 7621, 726139 (2009).
Karimaghaloo, Z. et al., "Intensity-based registration of prostate brachytherapy implants and ultrasound," IEEE Int. Symposium Biomed Imaging: 780-783 (2008).
Karimaghaloo, Z. et al., "Intra-operative localization of brachytherapy implants using intensity-based registration" 7th imaging Symposium of the Imaging Network of Ontario, poster, (2008). Call for Abstracts for Poster Presentation, Imaging Network Ontario, 7th Imaging Symposium, (Sep. 29 to Oct. 1, 2008).
Proceedings of 7th Imaging Symposium of the Imaging Network of Ontario, (Sep. 29 to Oct. 1, 2008), (cover page, p. 1, and p. 86).

* cited by examiner

*Primary Examiner* — Michelle L Le
(74) *Attorney, Agent, or Firm* — Stephen J. Scribner

(57) ABSTRACT

Provided are methods and systems for registering image data from two imaging modalities, to produce an image having features from both imaging technologies. In particular, the methods and systems relate to intensity-based registration of the image data. The imaging modalities may be, for example, ultrasound and x-ray, magnetic resonance imaging, or a pre-operative plan.

30 Claims, 6 Drawing Sheets

MARKER LOCALIZATION USING INTENSITY-BASED REGISTRATION OF IMAGING MODALITIES

RELATED APPLICATIONS

This application claims the benefit of the filing date of U.S. Provisional Patent Application No. 61/202,354, filed on Feb. 20, 2009, the contents of which are incorporated herein by reference in their entirety.

FIELD OF THE INVENTION

This invention relates to methods and systems for registering image data from two imaging modalities, to produce an image having features from both imaging technologies. In particular, the methods and systems relate to intensity-based registration of the image data. The imaging modalities may be, for example, ultrasound and X-ray or magnetic resonance imaging.

BACKGROUND

Ultrasound and X-ray are powerful imaging technologies that have found widespread use in clinical settings and in other applications such as inspection and examination of materials. Each technology has its strengths in producing images of different types of materials, and accordingly the use of either technology for a given application is often determined on this basis. However, in applications involving diverse materials it may be advantageous to use both techniques, so to acquire images of diverse features of interest. For example, certain medical procedures, such as brachytherapy, would benefit from the combined use of ultrasound and X-ray imaging.

Brachytherapy involves the placement of radioactive pellets or "seeds" into or adjacent cancerous tissue of a patient. Brachytherapy makes it possible to treat the cancer with a high total dose of radiation in a concentrated area in a short period of time, and at the same time spare healthy tissues the treatment with radiation. The key to successful brachytherapy is the accurate placement of the seeds. However, faulty needle and seed placement often cause an insufficient dose to the cancer and/or inadvertent radiation of healthy tissues. The ability to perform dosimetry optimization during the procedure could change the standard of care in brachytherapy, but such function is not available today and it is unfortunate that implants are currently performed without an explicit dosimetry evaluation in the operating room. Generally, dosimetric analysis requires precise localization of the implanted seeds in relation to the cancerous tissue and surrounding anatomy.

Brachytherapy has become the predominant treatment option for early stage prostate cancer. The procedure entails permanent implantation of radioactive seeds into the prostate to eradicate the cancer with ionizing radiation. In the case of prostate cancer, inadvertent radiation of the rectum, urethra or bladder through incorrect seed placement may result in adverse side effects such as rectal ulceration, incontinence, and painful urination.

Prostate brachytherapy is typically performed with transrectal ultrasound (TRUS) guidance that provides adequate real-time visualization of the prostate but not of the implanted seeds. Despite significant efforts, localization of seeds directly from TRUS has not been clinically practical or robust. C-arm fluoroscopy is often used for gross visual assessment of the implant but it cannot show the prostate. Recently, accurate reconstruction of seeds from fluoroscopy has become possible [2-5].

In specially-equipped operating rooms, computed tomography (CT) imaging [6] or cone beam CT [7] imaging is available. Because the shortcomings of TRUS and X-ray offset each other, quantitative dosimetry could be performed with spatial registration of the two. In order to register TRUS and fluoroscopy, Zhang et al. [8] suggested affixing radio-opaque fiducials to the TRUS probe, thereby permanently altering standard clinical equipment. Jain et al. [2] proposed precision machined fiducial structure calibrated to the needle guide template. Gong et al. [9] used needle tips as fiducials for the registration. For a variety of reasons specific to the brachytherapy workflow, fiducial-based approaches are not sufficiently reliable or clinically practical. Su et al. [3] and Tutar et al. [4] suggested point-based registration between seeds segmented and reconstructed in both fluoroscopy and TRUS. The generally poor quality of TRUS (due to noise, speckle, acoustic decoupling, calcifications masquerading as seeds, shadowing, multiple reflections, etc.) makes seed segmentation prone to error, causing instable registration performance.

SUMMARY

Described herein is a method for combining ultrasound image data and X-ray, MRI, or pre-implant plan image data of a material containing a plurality of markers, comprising: processing ultrasound images to construct a first volume, or to generate at least one first 2D projection, the volume or projection including at least a portion of the markers; processing X-ray images, MRI images, or pre-implant plan images to construct a second volume, or to generate at least one second 2D projection, the volume or projection including at least a portion of the markers; applying 3D intensity-based registration, or a derivative thereof, to align the markers in the first and second volumes, or to align the markers in the first and second 2D projections, to produce a combined image.

Also described herein is a method for combining ultrasound image data and X-ray, MRI, or pre-implant plan image data of a material containing a plurality of markers, comprising: processing ultrasound images to construct a first volume, the first volume including at least a portion of the markers; processing X-ray images, MRI images, or pre-implant plan images to construct a second volume, the second volume including at least a portion of the markers; applying 3D intensity-based registration, or a derivative thereof, to align the markers in the first and second volumes, to produce a combined image.

Also described herein is a method for combining ultrasound image data and X-ray, MRI, or pre-implant plan image data of a material containing a plurality of markers, comprising: processing ultrasound images to construct a first volume, the first volume including data corresponding to at least a portion of the markers; processing X-ray images, MRI images, or pre-implant plan images to construct a second volume or to construct a three dimensional (3D) point set, the second volume or 3D point set including data corresponding to at least a portion of the markers; applying 3D intensity-based registration, or a derivative thereof, to align data corresponding to the markers in the first and second volumes or the first volume and the 3D point set, to produce a combined image.

Processing ultrasound images may comprise filtering the images using an analysis with respect to space or frequency. Filtering the images may include applying at least one of a statistical analysis, a stochastic analysis, a fractal analysis, a wavelet analysis, a spectral analysis, a beam profile analysis, and array processing. Filtering the images may include applying at least one of window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering.

Processing X-ray images or MRI images may comprise filtering the images using an analysis with respect to space or frequency. Filtering the images may include applying at least one of a statistical analysis, a stochastic analysis, a fractal analysis, a wavelet analysis, a spectral analysis, and array processing. Filtering images may include applying at least one of window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering.

Processing ultrasound images and/or processing X-ray or MRI images may include filtering only a region of interest selected from the ultrasound images and/or the X-ray or MRI images. Processing pre-implant plan images may comprise applying an imaging-blurring filter.

Also described herein is a method for combining ultrasound image data and X-ray, MRI, or pre-implant plan image data of a material containing a plurality of markers, comprising: projecting an ultrasound volume to generate at least one first 2D projection, the first projection including at least a portion of the markers; processing X-ray images, or projecting X-ray images, MRI images, or pre-implant plan images to generate at least one second 2D projection, the processed X-ray image or the second projection including at least a portion of the markers; applying 2D intensity-based registration, or a derivative thereof, to align the markers in the first 2D projection and the processed X-ray image; or to align the first and second 2D projections, to produce a combined image.

Projecting ultrasound images may comprise filtering the images using an analysis with respect to space or frequency. Filtering the images may include applying at least one of a statistical analysis, a stochastic analysis, a fractal analysis, a wavelet analysis, a spectral analysis, a beam profile analysis, and array processing. Filtering the images includes applying at least one of window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering.

Processing X-ray images or projecting X-ray or MRI images may comprise filtering the images using an analysis with respect to space or frequency. Filtering the images may include applying at least one of a statistical analysis, a stochastic analysis, a fractal analysis, a wavelet analysis, a spectral analysis, and array processing. Filtering the images may include applying at least one of window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering.

Projecting ultrasound images and/or processing X-ray images or projecting X-ray or MRI images may include filtering only a region of interest selected from the ultrasound images and/or the X-ray or MRI images. Projecting pre-implant plan images may comprise applying an imaging-blurring filter.

Also described herein is a method for assessing marker placement in the anatomy of a subject during a medical intervention, comprising: using the methods described above to produce a combined image; and assessing marker placement in the subject's anatomy based on the combined image.

In the above methods, the markers may be radioactive seeds and/or surgical clips. In one embodiment, the images may be associated with a medical intervention. The images may be associated with a brachytherapy procedure. In one embodiment, the brachytherapy procedure may be associated with treating prostate cancer.

Also described herein is programmed media for use with a computer and with ultrasound image data and X-ray, MRI, or pre-implant plan image data, the image data pertaining to a material having a plurality of markers, the programmed media comprising: a computer program stored on storage media compatible with the computer, the computer program containing instructions to direct the computer to perform one or more of: process ultrasound images to construct a first volume, the first volume including at least a portion of the markers; process X-ray images, MRI images, or pre-implant plan images to construct a second volume, the second volume including at least a portion of the markers; apply 3D intensity-based registration, or a derivative thereof, to align the markers in the first and second volumes, to produce a combined image; and output an image including markers.

Also described herein is programmed media for use with a computer and with ultrasound image data and X-ray, MRI, or pre-implant plan image data, the image data pertaining to a material having a plurality of markers, the programmed media comprising: a computer program stored on storage media compatible with the computer, the computer program containing instructions to direct the computer to perform one or more of: project an ultrasound volume to generate at least one first 2D projection, the first projection including at least a portion of the markers; process X-ray images, or project X-ray images, MRI images, or pre-implant plan images to generate at least one second 2D projection, the processed X-ray image or the second projection including at least a portion of the markers; apply 2D intensity-based registration, or a derivative thereof, to align the markers in the first 2D projection and the processed X-ray image; or to align the first and second 2D projections, to produce a combined image; and output an image including markers.

Also described herein is programmed media for use with a computer and with ultrasound image data and X-ray, MRI, or pre-implant plan image data, the image data pertaining to a material having a plurality of markers, the programmed media comprising: a computer program stored on storage media compatible with the computer, the computer program containing instructions to direct the computer to perform one or more of: process ultrasound images to construct a first volume, the first volume including data corresponding to at least a portion of the markers; process X-ray images, MRI images, or pre-implant plan images to construct a second volume or to construct a three dimensional (3D) point set, the second volume or 3D point set including data corresponding to at least a portion of the markers; apply 3D intensity-based registration, or a derivative thereof, to align data corresponding to the markers in the first and second volumes or the first volume and the 3D point set, to produce a combined image; and output an image including markers.

Also described herein is a system for generating an output image from ultrasound image data of a material and X-ray, MRI, or pre-implant plan image data of the material, the material having a plurality of markers, the system comprising: a computer; programmed media as described above; and hardware and/or software associated with one or more imaging modalities. The imaging modalities may be selected from an ultrasound device; an X-ray device, an MRI device; or a device associated with a pre-implant plan of the material.

BRIEF DESCRIPTION OF THE DRAWINGS

For a better understanding of the invention, and to show more clearly how it may be carried into effect, embodiments will now be described, by way of example, with reference to the accompanying drawings, wherein.

DETAILED DESCRIPTION OF EMBODIMENTS

Figure 1A:
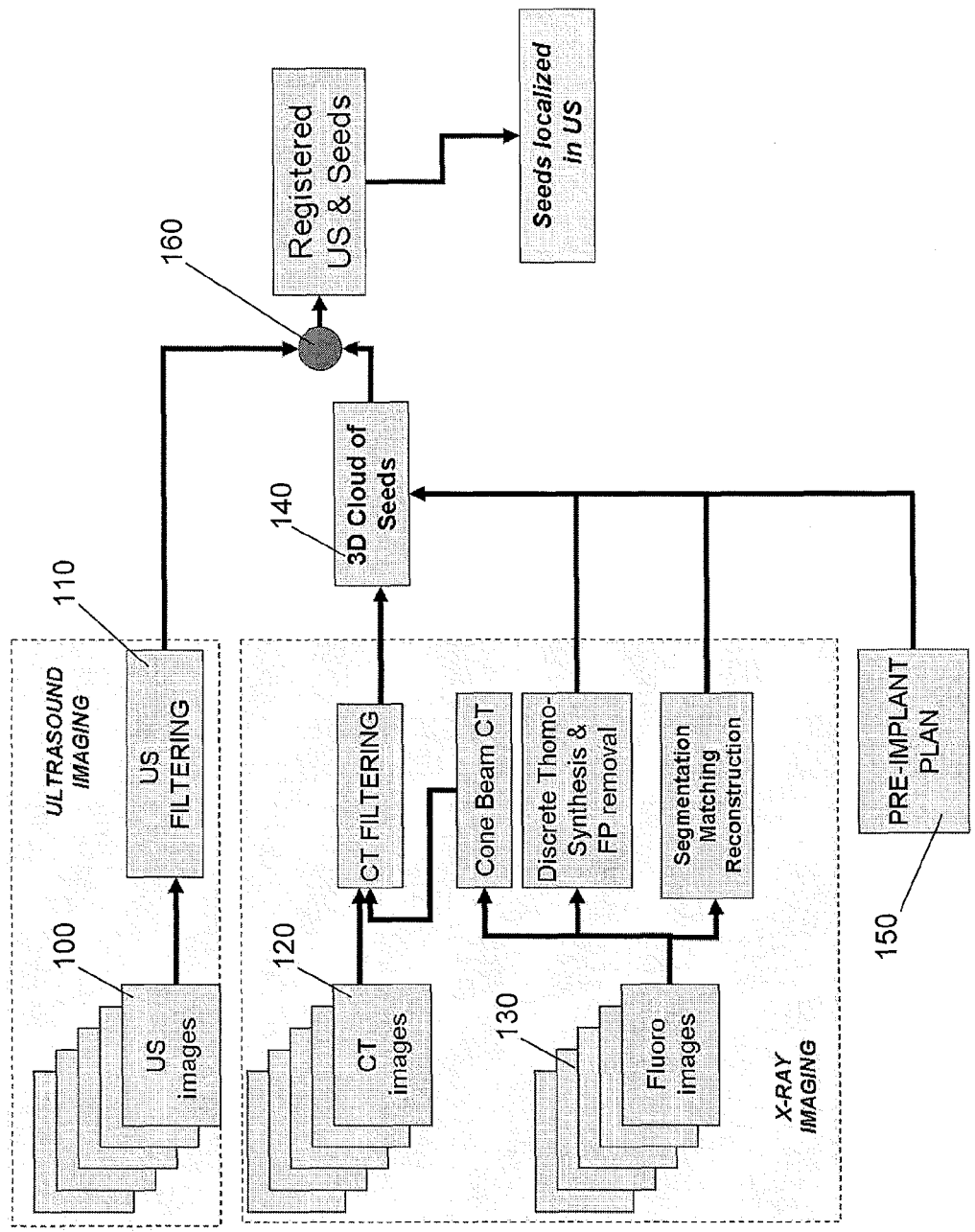
FIG. 1A is a generalized block diagram showing an intensity-based registration framework according to one embodiment, wherein images may be obtained from ultrasound (US) and computed tomography (CT), fluoroscopy, or a pre-implant plan.

Described herein is a method for combining data from two imaging technologies, so as to produce a resulting image that includes features provided by the two imaging technologies. Data from the two imaging technologies are combined by intensity-based registration of at least a portion of features, referred to herein as markers or seeds, common to the images of the two technologies. A block diagram of a generalized embodiment is shown in FIG. 1A. According to FIG. 1A, ultrasound images 100 are processed (e.g., filtered) 110 and subjected to intensity based registration 160 with X-ray image data, such as, for example, CT 120 or fluoroscopy 130, or image data obtained from a pre-implant plan 150. Although not shown in FIG. 1A, the ultrasound data may also be registered with MRI data, which is substantially interchangeable with CT data. The X-ray or MRI data may be subjected to processing prior to intensity-based registration, and several examples of such processing or shown in the figure. These are described in detail below.

Intensity-based registration techniques do not require prior segmentation, a substantial improvement over segmentation-based registration that usually requires some level of manual intervention and is hampered by segmentation errors. Intensity-based registration may use the entire volumes and thus both false positive and false negative appearances may average out. As used herein, the term "intensity" refers to the amplitude, pixel value, or probability score, or derivative thereof, such as a value derived from the intensity (e.g., image gradient), or combination thereof, of the markers or seeds in the images.

Imaging technologies that may be used in accordance with the embodiments described herein include, but are not limited to, ultrasound, e.g., TRUS, including A-mode, B-mode, M-mode, Doppler, and 3D, in combination with one of the following: (1) X-ray; including 2D X-ray, fluoroscopy, CT, or a 2D projection of a volume derived from CT; (2) MRI or a 2D projection of a volume derived from MRI; and (3) an image based on a pre-implant plan.

As used herein, the term "projection" refers to a 2D image generated from a volume by a ray-casting or ray-tracing technique, or a derivative thereof.

As used herein, the terms "pre-implant plan" and "pre-operative plan" refer to the planned distribution of markers or seeds in the material being imaged. For example, in a medical intervention, the pre-implant plan may be the clinician's planned distribution of brachytherapy seeds or markers in the tissue or organ under consideration. For example, the pre-implant plan for a brachytherapy procedure may provide a list of seeds in the coordinate frame of the brachytherapy system. If the pre-implant plan is executed perfectly, without any error or deviation from the plan, then the pre-implant plan will be identical to the cloud of seeds in the patient's anatomy. In this sense, as indicated in FIG. 1A, the pre-implant plan 150 is the same as the seed cloud 140 reconstructed from multiview X-ray fluoroscopy or CT. In actual clinical practice, however, there are deviations from the pre-implant plan and the seeds in the anatomy do not end up where they were planned. In this case, the pre-implant plan is no longer a perfect description of the seeds in the patient's anatomy. Still, assuming that the surgeon carried out the plan relatively faithfully, there is strong similarity between the pre-implant plan and the actual seed pattern in the prostate. Therefore, deformable intensity based registration may be used to map the pre-implant plan onto the ultrasound volume, wherein actual seed locations become marked in the ultrasound volume and the distribution of radioactive dose may be calculated. Use of pre-implant plan image data may include applying one or more filters to the data, such as, for example, an image-blurring filter (e.g., a Gaussian filter).

In one embodiment, the two imaging modalities are ultrasound and X-ray. These two technologies are typically used in clinical applications, such as for imaging anatomical sites during medical procedures and examinations. When using ultrasound and X-ray, approaches to combine the image data based on mutual information (MI) tend not to work, mostly because the anatomical structures being imaged are embedded in a low contrast environment with little distinctive information. However, as described herein, markers or seeds which may be resolved in both imaging technologies may be implanted in the site to be imaged. Information relating to the marker or seed location, which may be obtained from both imaging technologies, may then be used to register the ultrasound and X-ray image data. In contrast to prior attempts to combine ultrasound and X-ray image data, embodiments described herein include intensity-based registration.

As will be understood by one of ordinary skill in the art, images of the same material produced by each of the imaging modalities described herein will not exactly match each other. That is, the images produced by the different imaging modalities are not congruent. This is because of the physical properties of the material and how it interacts with the imaging modality to produce an image. In addition, in some applications images of a material obtained with two different modalities may not be obtained simultaneously, and any change in the material from when one imaging modality is used to when the next imaging modality is used will contribute to the lack of congruency in the images. The methods described herein include rigid registration, wherein any such incongruency of the images is disregarded in aligning the images. The methods described herein also include deformable registration, wherein the image data is adjusted to overcome or compensate for any incongruency. Rigid registration requires less computation and may be preferred in applications where rapid registration is required. Deformable registration begins with rigid registration, and then performs further iterations of the registration by adjusting the data to improve the fit. However, deformable registration requires more computation and is slower than rigid registration.

As used herein, the terms "marker" and "seed" are interchangeable and refer to a feature in a material that may be resolved with an imaging technology. Markers or seeds may include a feature already present in the material, such as an inherent part of the material, a feature implanted in the material, or combinations thereof. Markers or seeds may be manmade or naturally occurring. For example, a marker may correspond to particular material such as a specific type of cell or tissue, or a radioactive seed as used during a brachytherapy procedure, a surgical clip, a marker used to delineate a surgical margin, or an encapsulant for drug or gene vector release. A marker may be a labelled or tagged antibody designed for a specific type of cell or tissue.

In one embodiment, intensity-based registration is carried out using a volume-to-volume technique. Volume-to-volume handles scenarios where seeds are reconstructed into a continuous gray-scale volume, such as true CT or cone beam computed tomography volume. Volume-to-volume also allows for a gray-scale volume to be binarized, where each seed may be represented by more than one white voxel. Such volumes result from fluoroscopy reconstructions where seeds are considered to have length and direction. Since voxel intensity is used, an interpolator is used to evaluate moving volume intensities at non-pixel positions after applying the spatial transformation in each cycle of iteration. For this reason, the continuous TRUS is considered as the moving volume and the binarized seed cloud as fixed volume. For the first registration, the transformation parameters are initialized with an initial guess, discussed below. Then, a similarity measure evaluates the degree of matching between the transformed moving volume and the fixed volume. The measure may be, for example, mutual information or normalized correlation.

In one example of the volume-to-volume technique, the Mattes mutual information (MMI) is used. The MMI estimates a probability density function (PDF) uniformly distributed over the intensity interval. Calculations are based on the method of Mattes et al. [14, 27] where the probability density distributions are estimated using Parzen histograms. Compared to standard Mutual information, the technique involves initializing a random number generator that selects a sample of voxels used for estimating the volume histograms and the joint histogram. A feature of MMI is that it uses only two parameters: the number of samples used to estimate the PDF, and the number of histogram bins used to calculate the entropy. In one embodiment, the number of histogram bins was empirically set to 50 and the number of samples used was set to 10% of the total number of voxels making up the fixed volume. For comparative purposes, the normalized correlation (NC) was also tested. Voxel values were taken from the fixed volume; their positions were mapped to the moving volume and resulted in general in non-pixel positions on it. Values at the non-grid positions of the moving volume were interpolated using a user-selected interpolator. The correlation was normalized by the autocorrelations of both the fixed and moving volumes. Let Img1 and Img2 be the fixed and moving volume, respectively. NC computes the voxel-wise cross-correlation and normalizes it by the square root of the autocorrelation. Using a simple 2D image example:

$$NC = -1 \times \frac{\sum_{i=1}^{N} Img1_i \cdot Img2_i}{\sqrt{\sum_{i=1}^{N} Img1_i^2 \cdot \sum_{i=1}^{N} Img2_i^2}} \quad (1)$$

where Img1, and Img2, are the $i^{th}$ pixels in the two images and N is the number of pixels considered. The −1 factor is used to make the metric optimal when its minimum is reached. The optimal value of the metric is then −1. A misalignment between the images results in small measurement values. This metric produces a cost function with sharp peaks and well-defined minima. The above metrics work identically for volumes. The number of spatial samples may be set empirically, e.g., to 50.

In the case of the prostate, after TRUS imaging the probe is retracted from the rectum, to avoid blocking seeds during fluoroscopy imaging. This causes the prostate to relax posteriorly, but usually without significant deformation. Practice guidelines specifically require slight rectal pressure, to mitigate deformation by probe translation during TRUS imaging. In this light, rigid registration should suffice. A 3D Euler transform of six parameters may be implemented, three parameters for the Euler angles that represent the rotation and three for the translational components. The center of rotation may be specified as the gravity center of the moving volume. Clinically, there is always an accurate and consistent initial guess for the registration. Standard patient positioning allows for estimating the main symmetry axes of the prostate, and alignment of the gravity centers of the TRUS volume and the seed cloud yields an accurate guess for translation.

One example of an evolution strategy that may be used is the "one plus one evolution strategy", denoted by (1+1)-ES. The step size adaptation may be performed according to a rule, such as, for example: if less than 20% of the generations are successful, then decrease the step size for the next generation; if more than 20% are successful, and then increase the step size in order to accelerate convergence. This adaptation is done for every N−LR generations, where N is the number of parameters to be optimized and LR is a constant which here is equal to one. All parameter values were set to default with the maximum number of iterations set to 100 and the minimum value for the Frobenius norm of the covariance matrix set to 0.0015. If the value is smaller than this value, the optimization process will stop even before it hits the maximum iteration. The registration parameters were assigned initial weights corresponding to a 1 degree to 1 mm ratio for rotations and translations respectively. Of course, other values may be assigned to these parameters as desired for a given application or analysis.

Lastly, as TRUS and fluoroscopy are both likely to be spotted with false positives, the registration could be trapped in local minima. To counteract this potential problem, the registration may be restarted two or more times, each time slightly changing the initial pose (e.g., ±10% of last optimized parameter value), and then taking as a final solution the smallest root mean square results of the convergence optimizations.

Figure 1B:
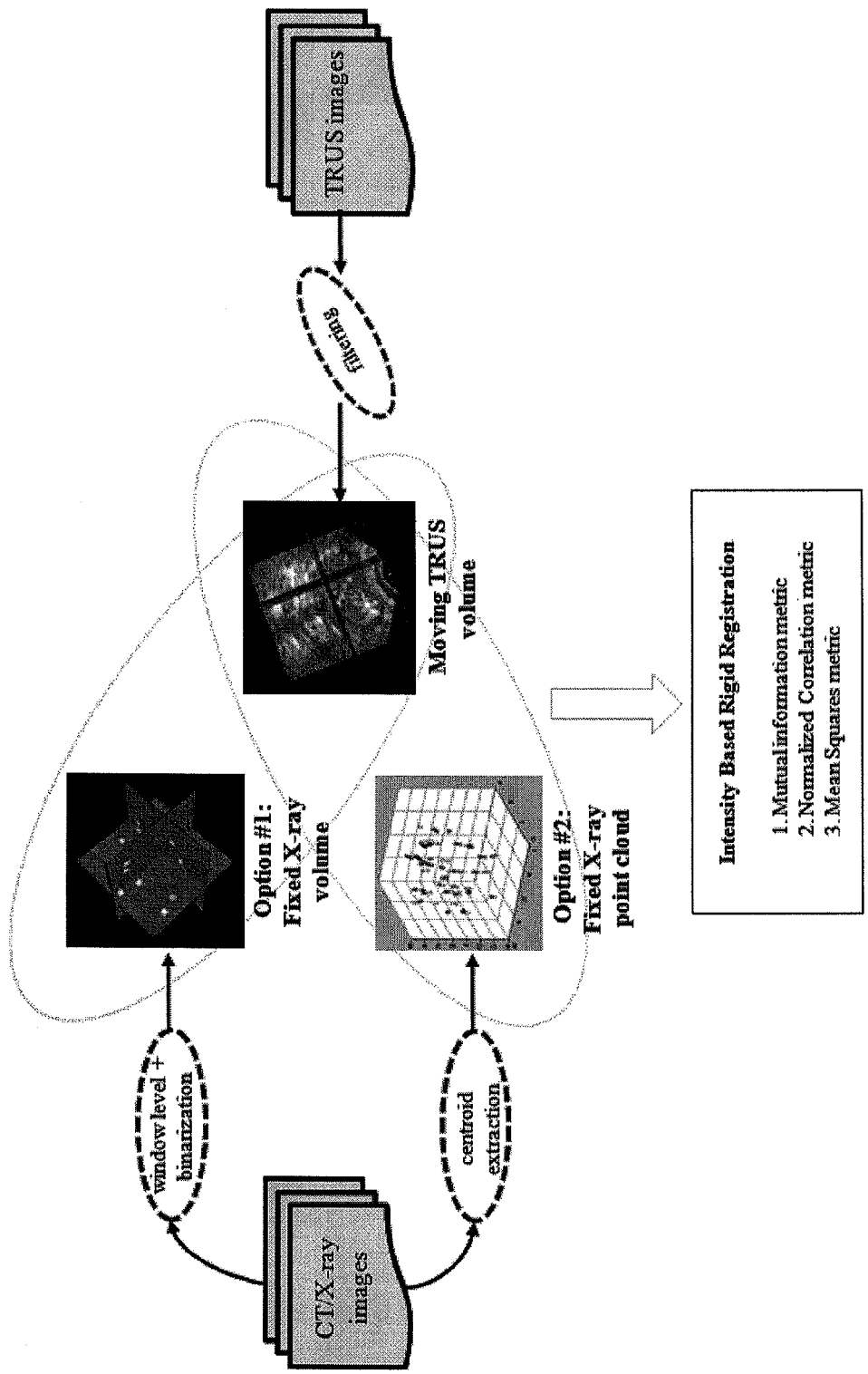
FIG. 1B is a block diagram showing intensity-based registration wherein TRUS images are filtered and compounded into a 3D volume. Seeds are reconstructed from either CT or fluoroscopy, either as a binary volume for volume-to-volume registration, or as a set of points, for point-to-volume registration, using mutual information, normalized correlation, or mean squares metrics.

An alternative to intensity-based volume-to-volume registration is intensity-based point-to-volume registration (see FIG. 1B). Point-to-volume registration employs an algorithm that maps a discrete 3D point set from CT, fluoroscopy, MRI, or CT-PET (positron emission tomography) to a moving TRUS volume, moving MRI volume, or moving CT volume. The goal of point-to-volume registration is to find the set of parameters of the transformation that optimizes a specified metric. In point-to-volume, the 3D point cloud is considered as a fixed volume and the TRUS as a moving volume, and a transformation that maps the moving volume to the fixed volume with maximum similarity is sought. To each point in the cloud a voxel value is assigned and thus a black volume sparsely spotted with single white voxels is created. Each seed is represented by exactly one white voxel. In the embodiments described herein, two metrics were tested for point-to-volume: normalized correlation and mean squares metric (MS), the latter computing the square difference between the average moving volume intensity for an inside point and the average moving volume intensity for an outside point. The optimal value of the metric is zero. Poor matches between the images result in large values of the metric. The metric is not difficult to compute and has a relatively large capture radius. The number of pixels considered, N, may be set to the image size.

$$MS = \frac{1}{N} \sum_{i=1}^{N} (Img1_i - Img2_i)^2 \quad (2)$$

An inside point is defined as a point for which the corresponding value (in the point set node) is negative. An outside point is defined as a point for which the corresponding value (in the point set node) is positive. The transform and optimizer are kept the same as described in the above for volume-to-volume. Generally, point-to-volume is designed for schemes where each seeds is reconstructed into a single point, and seeds are represented as a list of points. To demonstrate the effectiveness of the methods described herein, they have been applied to ultrasound (US) and X-ray data of biological tissue; specifically, for use during treatment of prostate cancer using brachytherapy. As described below, the radioactive seeds implanted in the prostate during the procedure are features which provide enough information in both imaging technologies for intensity-based registration, thereby providing enough information for a technique such as MI to be used. The methods described herein thereby avoid problems such as noise, artifacts, and false positive appearances typically experienced when transrectal ultrasound (TRUS) is used alone. In initial studies conducted on a phantom prostate, intensity based registration between TRUS and CT/fluoroscopy imaging of prostate implants produced excellent results: Target reconstruction error (TRE) was consistently below clinical threshold, capture range was significantly larger than the initial guess guaranteed by the clinical workflow, robustness to false positive seed appearances was very good, and temporal performance was adequate. In contrast to all previous attempts to register US and fluoroscopy, the methods described herein perform the registration accurately, robustly, and automatically, and do not require pre-segmentation, user intervention, fiducials, or any auxiliary instrumentation.

In one embodiment, the full original ultrasound signal volume is used for registration, without any forced data reduction. One or more filters are applied that exploit regularities in the ultrasonic signatures of the seeds or markers and produce a probabilistic volume of "seedness". These enhance the features of true seeds, that is, to suppress artifacts and false positive appearances. The optimal choice and order of filters may vary depending on the contents of the ultrasound volume to be registered. One embodiment for brachytherapy uses recursive thresholding and phase congruency, followed by rigid body registration based on mutual information. By changing the geometry of the reflector according to the shape and dimensions of brachytherapy seeds, the expected phase signature of seeds that can be recognized in an appropriately filtered ultrasound volume may be determined.

As noted above, pre-processing of image data may be required. For example, US, X-ray, and MRI data may be pre-processed with at least one filter based on an analysis with respect to space and/or frequency. Such an analysis may include one or more of:
 (i) a statistical analysis;
 (ii) a stochastic analysis;
 (iii) a fractal analysis;
 (iv) a wavelet analysis;
 (v) a spectral analysis; and
 (vi) array processing.
The result of the analysis may be a probability map, a probability score, intensity information, or a derivative thereof.

Examples of filters suitable for US, X-ray, and MRI data include, but are not limited to, window-level scaling, binary thresholding, a noise reduction filter, thresholding, averaging, median filtering, speckle reduction, diffusion filtering, anisotropic filtering, phase congruency, phase symmetry, gradient filtering, and contrast enhancement filtering. These may be used alone, or in various combinations, such as in series, parallel, or series-parallel combinations.

In addition to the above, US data may also be subjected to beam profile filtering optionally in combination with any of the above.

As applied to prostate brachytherapy, the methods described herein provide major improvements in current practice of prostate cancer brachytherapy. Examples of such improvements include: (1) practical C-arm fluoroscopy for safe, simple, and robust intra-operative localization of brachytherapy sources relative to the prostate; (2) intra-operative dosimetry and implant optimization; and (3) exit dosimetry before the patient is released from the procedure room. Additionally, C-arm fluoroscopy-based exit dosimetry may also obviate CT-based post-implant dosimetry in the future. These benefits are expected to apply to all brachytherapy in general.

While the embodiments described herein relate primarily to prostate brachytherapy, it will be appreciated that the invention is not limited thereto. The embodiments may be used for brachytherapy procedures in other biological tissues and/or organs. The brachytherapy may include, but is not limited to, high dose rate, low dose rate, and pulse dose rate brachytherapy. Further, the methods described herein may be applied to the detection, diagnosis, treatment, and/or assessment of cancer or other diseases in any biological tissues and/or organs, provided that suitable markers or seeds are available to be resolved with the imaging technologies used. The markers or seeds, which may be any of the types discussed above, in any combination, may be already present in the tissues, or they may be implanted in the tissues prior to or during the diagnosis, treatment, and/or assessment. Such biological tissues and organs may include, but are not limited to, female genital tract (ovary, fallopian tube, uterus, cervix and vagina), male genital tract (prostate and testis), urinary tract (kidney, ureter and prostate gland), mediastinum and heart, gastrointestinal tract (small and large intestines, liver, pancreas, gallbladder and biliary system), breast, skin, nervous system, endocrine organs (thyroid gland, adrenal gland), head and neck region, lymph nodes, soft tissue, respiratory system (including lung). Embodiments of the invention may also be used for detection, diagnosis, and/or assessment of tissue abnormalities including pathological abnormalities other than cancer, such as, but not limited to, benign tumours, infection, abscess, necrosis, and infarcts.

Insofar as the methods described herein exploit the spectral signature of ultrasonic reflections produced by "solid objects", i.e., seeds or markers, inside the material being imaged, it will be appreciated that the methods may be applied to any clinical application where suitable reflecting objects are present or are used, wherein registration of real-time US to other imaging modalities (such as, for example, CT or MRI) or to statistical anatomical atlases is required. For example, the reflectance of the pelvis may be applied in US-guided total hip replacement surgery, or the reflectance of bone fragments may be applied in US-guided bone fracture reduction (e.g., of the wrist, shoulder, etc.). In a similar manner, reflectance of the vertebra may be used in US-guided nerve root blocks, facet joint injection, and epidural injections.

As used herein, the term "biological tissue" is intended to be inclusive of any tissue derived from an organism or part thereof, as well as a cell culture and a tissue culture. The biological tissue may be living or dead, and an analysis as described herein may be carried out on biological tissue in vivo or in vitro.

Embodiments of the invention may also be used for inspection and/or assessment of non-biological materials provided that suitable markers or seeds are available to be resolved in the imaging technologies used. Such applications may include inspection of materials for manufacturing and/or structural defects, analysis of effects of stress/strain on machine components, and detecting failure of machine components, in manufacturing, research, and industries such as transportation and aerospace. The markers or seeds may be already present in the materials (e.g., as an inherent feature of the materials), or they may be implanted in the materials prior to or during the inspection and/or assessment.

Embodiments of the invention may also be used for inspection and/or assessment of combinations of biological tissues and non-biological materials provided that suitable markers or seeds are available to be resolved in the imaging technologies used. For example, the methods may be used during surgery to ensure accurate placement of prosthetic devices, and/or after such procedures to confirm the placement and/or monitor the position or status of the implanted device. Application of the embodiments to other biological tissues and non-biological materials may require the implantation of markers or seeds the tissues or materials, or the tissues or materials may already include features which may serve as markers or seeds.

The embodiments described herein may be implemented in software, and may, for example, be made available as an add-on to imaging systems that are commercially available or currently in use, without adding auxiliary instrumentation and without imparting alterations in the basic clinical process. These features make it suitable for rapid and wide scale use, thus providing an immediate positive impact upon the thousands of patients undergoing brachytherapy and other relevant medical procedures every year.

The embodiments described herein may be implemented in a system including computer hardware, such as a dedicated computer-based system for use with imaging modalities to combine images from the imaging technologies by intensity-based registration of markers or seeds common to the images of the two modalities. The system may further include hardware associated with one or more imaging modalities, such as, for example, an ultrasound device, an X-ray device (e.g., fluorpscopy, CT), an MRI device, or a device related to a pre-implant plan of the material being imaged.

The following non-limiting examples are provided to further illustrate the invention.

Example 1

Evaluation of Ultrasound Filtering for Localization of Brachytherapy Seeds

Figure 1C:
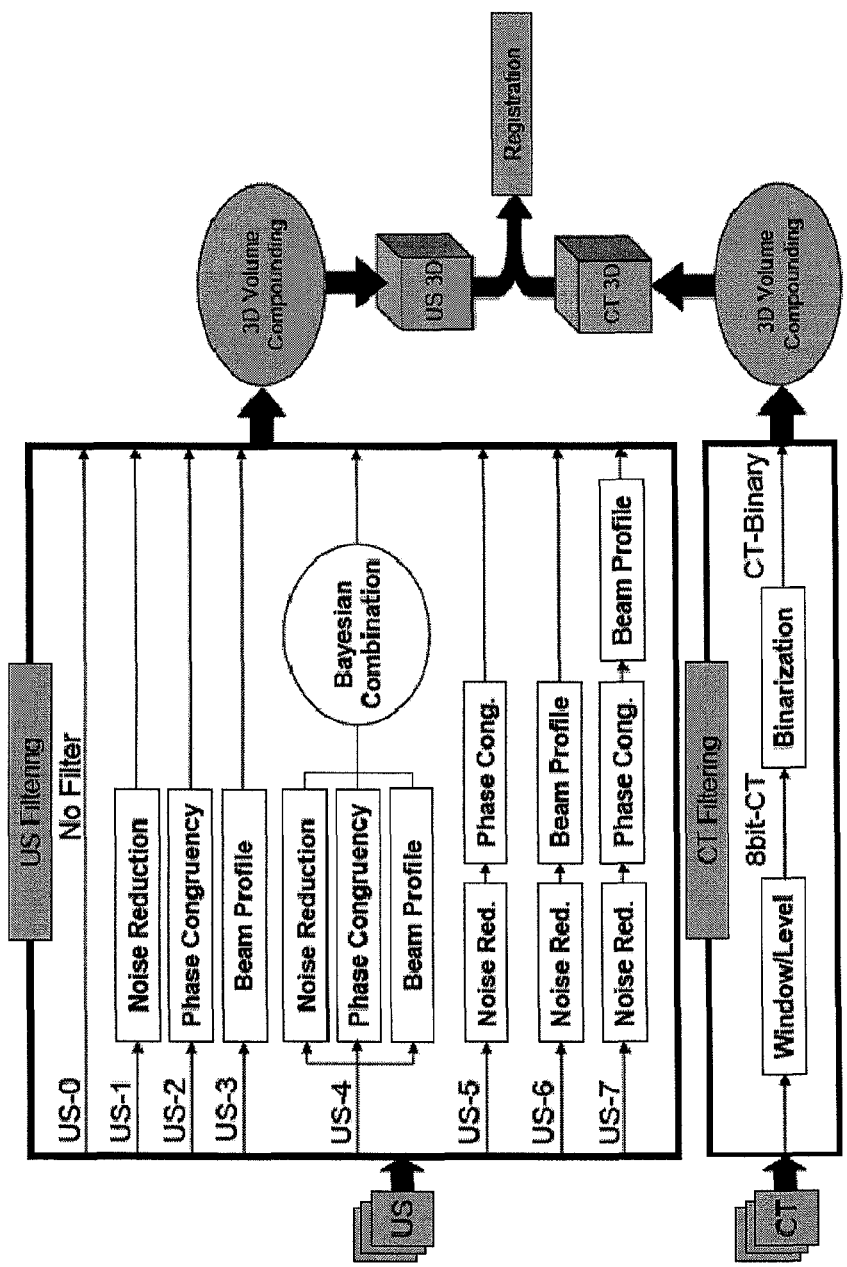
FIG. 1C is a block diagram showing an intensity-based registration framework according to an alternative embodiment, wherein images are obtained from US and CT. The US frames may be processed by one or more of seven exemplary filters. In this embodiment the CT frames are scaled and optionally binarized. The volumes are compounded and supplied to the MI registration engine.

An embodiment for localization of brachytherapy seeds based on ultrasound (TRUS) and X-ray image (computed tomography, CT) data will now be described with reference to FIG. 1C, which shows the basic framework. Briefly, the TRUS and X-ray reconstruction data were filtered, compounded to volumes, and then mutual information based multi-modal registration was applied. According to this embodiment, the CT/fluoroscopy reconstruction is pre-created in one of several ways. For example, intraoperative CT may available [6], cone beam tomography reconstruction may be applied with specialized tables and advanced fluoroscopy units [7], and discrete shot fluoroscopy may be used, which allows for both tomosynthesis, producing a coarse tomographic volume [5], and segmentation-based seed matching, yielding a cloud of seeds (i.e., a binary volume) [2]. Any of these may be used.

1.1. Filtering of X-ray Data

In this embodiment, filtering may be applied to the CT data. Because seeds are prominent in CT and fluoroscopy, it is not essential that the entire data be used. For example, a region of interest may be clipped, and subjected to filters such as window-level scaling and optional binary thresholding, as shown in FIG. 1C. In the case of true CT, either the slices (as in FIG. 1C) or the whole volume may be filtered, but the difference is not significant as seeds dominate the scene. Filtering is used to suppress the soft tissue features in the image and highlight desired features, such as seeds or surgical clips, in the X-ray image. Filtering may ensure that the seeds or markers dominate through the intensity domain.

1.2. Filtering of Ultrasound Data

In this embodiment, filtering may be applied to the ultrasound data. Various filters may be employed as discussed above, and selected examples of such filters were used on the TRUS data to test and compare their ability to suppress artifacts and enhance seed-like regions without explicit segmentation. For a baseline, no filter was used (US-0; see FIG. 1C). Examples of other filters that may be used include the following, with reference to FIG. 1C:

US-1: a noise reduction filter. Examples include, but are not limited to thresholding, averaging, median filtering, speckle reduction, diffusion filtering, anisotropic filtering, and phase symmetry filtering. These may be used alone or in any combination.

US-2: a phase congruency filter. Previously, Hacihaliloglu et al. used phase congruency (PCON) for detecting bone edges in ultrasound [10]. PCON evaluates features based on phase rather than amplitude information. Since it gives a measure of significance for each point invariantly to image brightness or contrast, a constant and uniform threshold can be applied to extract feature points from the phase information [11]. The PCON at each pixel of each image was calculated in order to measure phase symmetry. The more symmetrical the phase of a region is, the more likely it is to be a seed. The measure of symmetry was calculated as the weighted average resulting from even and odd symmetry filters. (At symmetry points, the absolute values resulting from even and odd symmetry filters are large and small, respectively.) For example, the MATLAB R® implementation of PCON from Kovesi (Peter Kovesi, The University of Western Australia, http://www.csse.uwa.edu.au) may be used.

US-3: a beam profile filter. This filter accounts for the fact that the ultrasound beam has finite thickness and single focus in the elevation plane. In one embodiment, the number of focal points in the lateral plane was set to two. Together, these make fidelity across the image non-uniform [12]. More weight may be given to the regions near the focal points and less to the ends of the image where the beam is less accurate.

US-4: parallel noise reduction, phase congruency, and beam profile filters. These were combined in a Bayesian model, where each filter independently estimated "seedness", and their results were combined as in [13].

US-5: noise reduction followed by phase congruency. As an alternative, phase symmetry may also be used.

US-6: noise reduction followed by beam profile filtering.

US-7: noise reduction, phase congruency, and beam profile filtering were cascaded.

It will be appreciated that other filtering techniques may be used. The filtering techniques may be used alone, or in any combination.

1.3. Registration of Ultrasound and X-ray Data

TRUS and fluoroscopy may be performed almost concurrently. Generally, TRUS and fluoroscopy are performed one after the other. This is because it is usually not possible to perform them concurrently, as the TRUS probe blocks the field of the fluoroscopy and obscures the implanted seeds. After TRUS, the probe is retracted from the rectum, so as not to block seeds during fluoroscopy. This may cause the prostate to sag, but usually without apparent deformation. In this case, rigid MI registration may be applied, based on an accurate initial approximation for the registration, which is a valid assumption supported by clinical observation. Consistent patient positioning allows for estimating the main symmetry axes of the prostate, and alignment of the gravity centers of the TRUS and CT/fluoro volumes yields an accurate estimation for the translation [2]. For example, the patient may be placed on the operating table and the C-arm is placed around the table in a consistent and predictable manner, to facilitate an accurate initial approximation for rotation. For translation, binary thresholding may be performed on both TRUS and CT data, the centers of gravity aligned, which produces an accurate initial translation, well within the capture range.

1.4. Experimental Data

Figure 2:
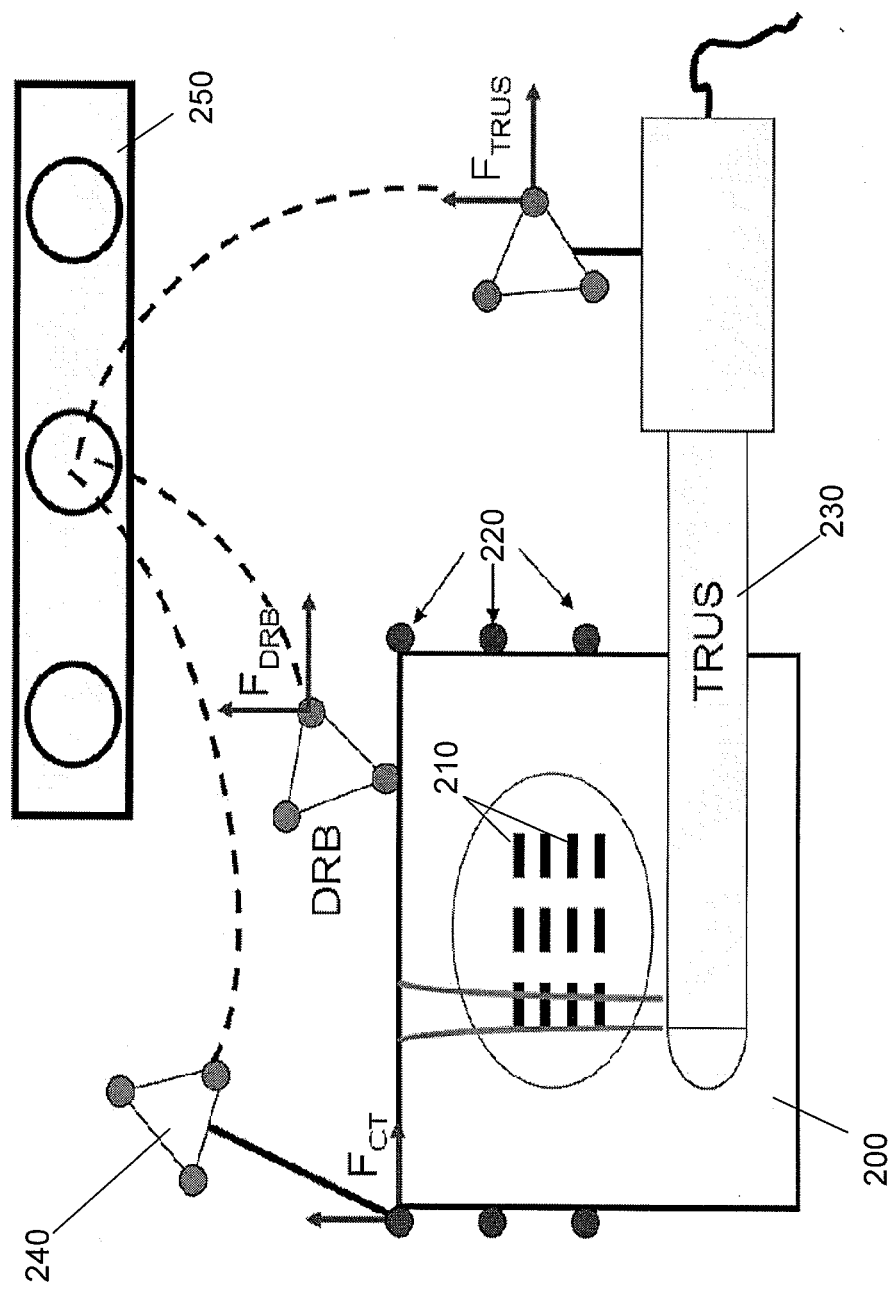
FIG. 2 is a block diagram showing coordinate transformations in an experimental ground truth phantom setup for brachytherapy. A calibrated pointer is used to register the CT fiducials to the dynamic reference body (DRB). The TRUS probe is tracked relative to the DRB.

FIG. 2 shows an experimental setup used to obtain ground truth phantom data. The process and notations are familiar from basic surgical navigation literature. A realistic implant in a phantom (ORS, Norfolk, Va.) 200 was performed with 48 seeds 210 (12 are shown in the figure), and a set six of 1 mm CT fiducials 220 was arranged on the container box. For example, two triplets of CT fiducials were placed on two opposite sides of the container, so that the gravity center of the fiducials approximately coincided with the center of the prostate, to maximize registration accuracy. The TRUS probe 230 was placed in the phantom 200. A CT volume with 0.3 mm pixel size and 0.6 mm slice thickness was then acquired. The six fiducials attached to the walls of the phantom were segmented. The CT fiducials were also localized with a calibrated pointer (Traxtal Inc., Toronto, ON) 240 and Certus optical tracker (NDI, Waterloo, ON) 250 with respect to the DRB coordinate on the phantom. Finally, the position of seeds segmented in CT images were transformed to the TRUS coordinate system, thereby defining the ground truth for the registration. To maximize registration and tracking accuracy, the fiducials and tracking bodies were arranged so that their centroids fell close to the center of the prostate.

1.5. Results

Perturbation was applied to the TRUS volume (i.e., moving image) and the registration was performed to bring the TRUS volume back to coincidence with the CT volume. The effects of the various TRUS pre-processing filters, shown in FIG. 1C, were tested extensively. In testing each filter, 30 registrations were accomplished starting from 30 different initial misalignments, randomly chosen from the range of 30 degrees for three-axis rotation and 10 mm for Cartesian translation. Registration was marked as a "failure" if the optimization algorithm did not converge after 200 iterations. The mean registration error and STD of the seeds were calculated from the difference between true and estimated seed positions, obtained from the ground truth and the registration, respectively. This measure served as the target reconstruction error (TRE). All registrations were performed using Mattes mutual information method [14] implemented in ITK 3.4 (National Library of Medicine, Insight Toolkit, http://www.kitware.com).

A set of registrations was carried out between TRUS and the 8-bit CT and another set between TRUS and binarized CT. As seeds dominate the scene inside the prostate and window-level scaling yields a near binary volume, the performances of the binary and the 8-bit filters were almost identical (see Table 1). Nonetheless, binarization was included to be compatible with all X-ray reconstruction techniques. All methods gave a mean seed registration error less than 1 mm which is well below the clinically acceptable threshold (the diameters of implant needles and seeds are about 2 mm and 1 mm, respectively.) There was an apparent trade-off between minimizing TRE and failure rate, but as all filters produced clinically excellent TRE, failure rate tends to tip the balance.

US-0 (No filtering): The pure US volume was used without any further preprocessing, yielding 0.66 mm TRE and 13% failure rate. This was considered as the baseline for the comparison of the first four TRUS filters.

US-1 (Noise reduction filter): TRE increased slightly, from 0.66 mm to 0.72 mm (the difference was not found to be statistically significant, p=0.11), but failure rate dropped from 13% to zero.

US-2 (Phase congruency filter): TRE did not change noticeably, but failure rate decreased from 13% to 6%.

US-3 (Beam profile filter): There was statistically significant improvement in TRE from 0.66 mm to 0.48 mm (p<0.05), while failure rate spiked up from 13% to 40%.

US-4 (Parallel Bayesian combination of noise reduction, phase congruency and beam profile filters): Compared to baseline, TRE went down slightly to 0.57 mm, while failure rate remained at 13%. These were not at all surprising numbers, for in a Bayesian model independent parameters tend to level out between their respective extremes. From the first four filters, the Bayesian scheme (US-4) seems optimal and was considered as the baseline in testing the remaining three filters.

US-5 (Sequence of noise reduction and phase congruency filters): There was no mentionable difference in TRE, but failure rate was halved.

US-6 (Sequence of noise reduction and beam profile filters): TRE went slightly up, but failure rate dropped to zero.

US-7 (Sequence of noise reduction, phase congruency and beam profile filters): TRE decreased slightly to from 0.57 mm to 0.52 mm, and failure rate was halved.

From the four sequential filters tested, US-7 seemed to yield the best performance. Altogether, simple noise reduction (US-1) yielded excellent TRE and zero failure rate. In fact, no filtering (US-0) also performed well (strong TRE, 13% failure rate) and with two slight "nudges" to the initial guess it would usually converge. Complex filters did not have much positive impact on TRE, while they tended to increase the failure rate. In retrospect, this is not surprising, because there is only very little tissue canvas to be seen between the seeds that dominate the intensity domain in both volumes.

TABLE 1

US images were preprocessed using one of the methods (US-0 to US-7), CT volume was compounded by either 8 bit or binary images.

| | CT-8 bit | | CT-Binary | |
|---|---|---|---|---|
| Methods | Mean ± Std mm | % of Failure | Mean ± Std mm | % of Failure |
| US-0 | 0.63 ± 0.18 | 17 | 0.66 ± 0.20 | 13 |
| US-1 | 0.73 ± 0.17 | 0 | 0.72 ± 0.17 | 0 |
| US-2 | 0.59 ± 0.21 | 6 | 0.65 ± 0.19 | 6 |
| US-3 | 0.49 ± 0.16 | 40 | 0.48 ± 0.17 | 40 |
| US-4 | 0.53 ± 0.22 | 13 | 0.57 ± 0.19 | 13 |
| US-5 | 0.65 ± 0.38 | 6 | 0.58 ± 0.18 | 6 |
| US-6 | 0.68 ± 0.17 | 0 | 0.61 ± 0.17 | 0 |
| US-7 | 0.50 ± 0.21 | 6 | 0.52 ± 0.20 | 6 |

For each chosen CT and US volume, registration was run 30 times using different random initial misalignments.
Mean and standard deviation of TRE and the failure rate per each trial are shown.

1.6. Handling of False Positives

Human prostates tend to present with false positive appearances such as double reflections and calcifications. These were simulated by masking out seeds from the CT volume. The triple-cascade filter (US-7) was run and the results compared to the baseline of US-0. Up to 15 seeds (31%) in the CT volume were masked out. For each trial, the masked seeds were picked randomly, repeated 30 times. For the sake of completeness, the registration was run for both 8-bit and binary CT (see Table 2). Robustness to false positives shows significant improvement over the baseline. For up to 31% false positives, a 13% failure rate was obtained for US-7 with about 1.05 mm TRE, while almost 43% of all registrations failed with the baseline filter. In these tests, it was beneficial to use a complex TRUS filter, although it is not yet certain which of the three filters in the cascade made the greatest contribution, or if the order of these filters matters. However, it is expected that the order of filters will not make a clinically noticeable difference in registration performance.

The US-7 filter took approximately 17 seconds per image and each registration took 1.5 minutes using an Intel core2, 2.46 kHz, dual-core computer.

Most modern brachytherapy units have an optically-encoded probe stepper that makes it possible to collect TRUS slices that overlap in the elevation direction. This feature allows compounding of very dense and jitter-free TRUS volumes, especially on units where RF ultrasound data is available in addition to conventional B-mode images. Using this feature, compounding may be performed first, and volumetric filtering applied before running the registration.

TABLE 2

False positive (FP) evaluation of the embodiment compared to the non-processed US volume. For each FP percentage, registration was run 30 times. Mean and standard deviation of TRE as well as the failure rate are shown. CT volume was compounded by either 8 bit or binary images.

| | CT-8 bit | | | | CT-Binary | | | |
|---|---|---|---|---|---|---|---|---|
| | US-7 | | US-0 | | US-7 | | US-0 | |
| FP % | Mean ± Std mm | % of Failure | Mean ± Std mm | % of Failure | Mean ± Std mm | % of Failure | Mean ± Std mm | % of Failure |
| 2% | 0.61 ± 0.25 | 6 | 0.67 ± 0.17 | 13 | 0.59 ± 0.24 | 6 | 0.68 ± 0.18 | 13 |
| 4% | 0.55 ± 0.23 | 6 | 0.69 ± 0.25 | 16 | 0.54 ± 0.21 | 6 | 0.66 ± 0.18 | 16 |
| 6% | 0.58 ± 0.27 | 10 | 0.72 ± 0.30 | 13 | 0.54 ± 0.23 | 10 | 0.64 ± 0.25 | 13 |
| 8% | 0.67 ± 0.32 | 17 | 1.21 ± 1.43 | 33 | 0.63 ± 0.22 | 17 | 0.88 ± 0.40 | 37 |
| 10% | 0.67 ± 0.25 | 10 | 0.79 ± 0.17 | 20 | 0.64 ± 0.19 | 10 | 0.73 ± 0.17 | 16 |
| 13% | 0.52 ± 0.27 | 20 | 0.71 ± 0.32 | 23 | 0.41 ± 0.23 | 20 | 0.60 ± 0.26 | 27 |
| 15% | 0.48 ± 0.23 | 13 | 0.67 ± 0.23 | 23 | 0.45 ± 0.25 | 13 | 0.64 ± 0.24 | 23 |
| 17% | 0.57 ± 0.17 | 23 | 0.72 ± 0.23 | 30 | 0.55 ± 0.17 | 20 | 0.66 ± 0.22 | 30 |
| 19% | 0.78 ± 0.32 | 13 | 1.31 ± 0.86 | 27 | 0.78 ± 0.24 | 13 | 1.02 ± 0.27 | 30 |
| 21% | 0.70 ± 0.24 | 6 | 0.82 ± 0.25 | 23 | 0.71 ± 0.21 | 6 | 0.85 ± 0.23 | 23 |
| 23% | 0.54 ± 0.30 | 13 | 0.64 ± 0.27 | 23 | 0.49 ± 0.29 | 13 | 0.58 ± 0.26 | 23 |
| 25% | 0.71 ± 0.22 | 17 | 0.82 ± 0.28 | 40 | 0.66 ± 0.19 | 17 | 0.82 ± 0.20 | 40 |
| 27% | 0.45 ± 0.29 | 6 | 0.55 ± 0.30 | 40 | 0.41 ± 0.30 | 6 | 0.44 ± 0.22 | 40 |
| 29% | 0.53 ± 0.29 | 17 | 0.72 ± 0.23 | 30 | 0.48 ± 0.22 | 13 | 0.51 ± 0.18 | 33 |
| 31% | 1.05 ± 0.25 | 13 | 0.95 ± 0.30 | 47 | 1.05 ± 0.26 | 13 | 1.06 ± 0.24 | 43 |

Example 2

Localization of Brachytherapy Seeds Using Phase Congruency Filtering of Ultrasound In this example the methods described above were used with phase congruency filtering of the ultrasound data. Based on the assumption that brighter areas in the image are more likely to contain seeds, all pixels with less than the average intensity of the US volume were coloured black. The average intensity was calculated for the pixels within the smallest box containing the prostate boundary. Then, the average was recalculated and the procedure was repeated. After these successive thresholdings, intensity values were resealed to lay between 0 and 1, thereby producing a set of intensity-based probability images.

2.1. Phase Congruency Method

Phase congruency [10] was adapted for pre-processing the US images to enhance the features of true seeds, i.e., to suppress artifacts and false positive appearances. Phase congruency is a method for evaluating features based on the phase rather than the amplitude information of images. Since the method gives a measure of significance for each point invariantly to image brightness or contrast, a constant threshold can be applied to extract feature points from the phase information. Hence a uniform threshold was applied for all images [11]. For extracting the seed-like regions from a single B-mode image, calculating the phase congruency of pixels provides useful information: the more symmetrical the phase of a region is, the more likely it is a seed. For calculating the phase congruency in the image, two filters were applied: an even symmetry filter and an odd symmetry filter. A measure of symmetry was calculated in each point based on the weighted average of coefficients resulting from applying these two filters. At symmetry points, the absolute value of the even-symmetry filter result is large and the absolute value of odd symmetry filter result is small. Thus, the measure of symmetry is defined as follows [17]:

$$PC(x) = \frac{\sum_o \sum_n W_o(x) \lfloor A_{no}(x) \Delta\Phi_{no}(x) - T_o \rfloor}{\sum_o \sum_n A_{no}(x) + \epsilon},$$

where $$A_n(x)\Delta\Phi_n(x) = e_n(x)\overline{\phi_e(x)} + o_n(x)\overline{\phi_o(x)} - |e_n(x)\overline{\phi_o(x)} - o_n\overline{\phi_e(x)}|$$

$$\overline{\phi_e(x)} = \frac{\sum_n e_n(x)}{E(x)} \quad \overline{\phi_o(x)} = \frac{\sum_n o_n(x)}{E(x)}$$

Here, o and n define the number of orientations and scales which are found empirically. In this example, scales and 6 orientations were used. $W_o$ is a weighting function, and $T_o$ is for noise compensation which is calculated from the maximum output that can be generated only by considering the noise in each orientation independently. The small term $\epsilon$ is to avoid division by zero. $e_n(x)$ and $o_n(x)$ are the results of applying even and odd symmetric filters, respectively, and $E(x)$ is the local energy function. As above, the MATLABR implementation of this algorithm provided by P. Kovesi was used.

2.2. Registration

A 3D rigid body registration was performed between the preprocessed US volume and the 3D model of seeds reconstructed from fluoroscopy. Since exact localization of the seeds from US images can not be achieved reliably, intensity-based registration was chosen rather than point based registration. Mutual information was used as the metric for registration.

2.3. Experimental Setup

The experimental setup is shown in FIG. 2. A standard brachytherapy training phantom (CIRS Inc, Virginia) was implanted with 49 non-radioactive seeds according to a clinically realistic implant plan. Para-sagittal US images of the phantom were captured using a linear probe operating at 6.6 MHz, and a Sonix RP machine (Ultrasonix, Richmond, Canada). A dynamic reference body (DRB) was attached to the US probe and one was attached to the phantom in a way that both DRBs were visible with an OPTOTRAK Certus camera (NDI, Waterloo, Canada) used as the tracking system.

Six small metal fiducials were attached to the corners of the phantom box, and their spatial position was measured with respect to the DRB on the phantom using a calibrated stylus. Since these fiducials were also visible in the CT images, the ground truth for the registration was obtained based on these fiducials.

2.4. Ultrasound Volume Reconstruction

During the scanning procedure, the position of the US probe was recorded by the tracking system with respect to the coordinate frame of the DRB on the phantom [12]. Following the earlier described pre-processing of the individual US images, based on tracking information, the images were compounded into a 3D volume using the method of Gobbi et al. [15].

2.5. Implant Reconstruction

In an actual clinical setting, implanted brachytherapy seeds are reconstructed intra-operatively from C-arm fluoroscopy. In this example, it was assumed that a reconstructed 3D model is available and it was simulated with binary CT data. CT images of the implanted phantom were obtained with a spacing of 0.43×0.43 mm of in-plane resolution and interpolated slice thickness of 0.625 mm. A constant threshold was applied to all images in a way that seeds were masked to white and everything else to black.

2.6. Results

Figure 3:
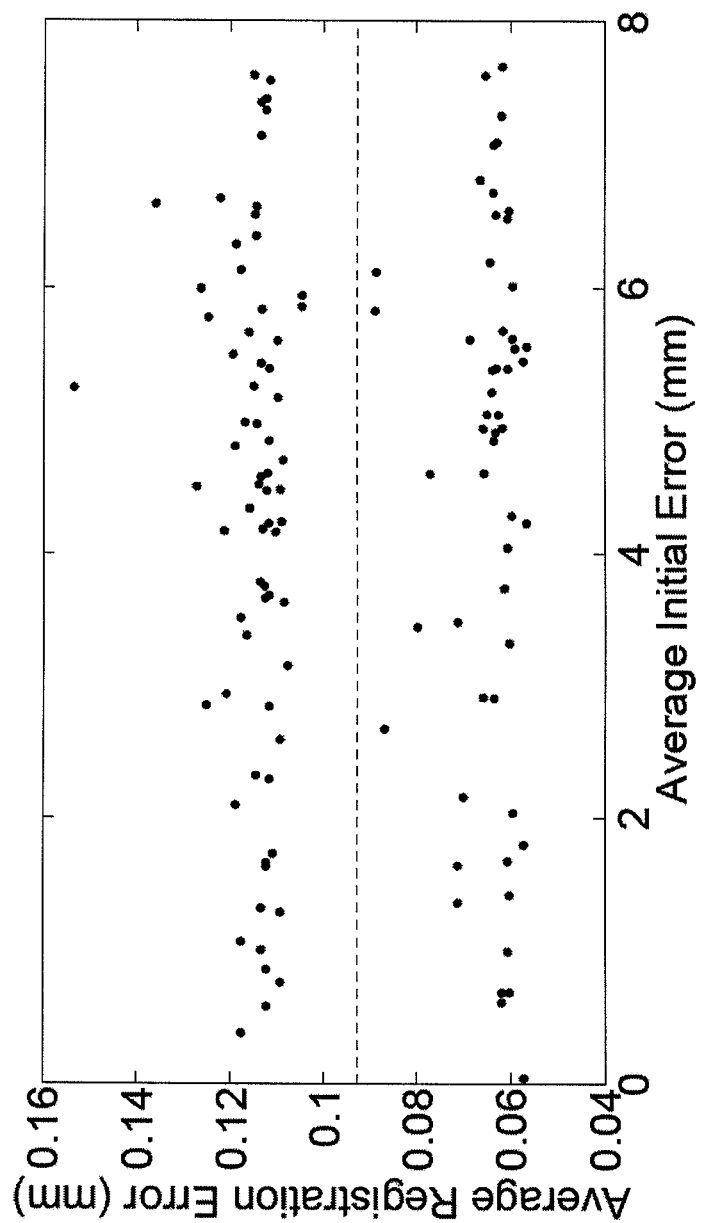
FIG. 3 is a plot showing the result of the registration of ultrasound and X-ray data using the experimental setup of FIG. 2 and phase congruency filtering of the ultrasound data.

For validation of the robustness of the registration, the CT and US volumes were misaligned (relative to the ground truth) by applying a random transformation (±10 degree for the rotation angle, ±5 mm for translation) to the US volume. The US volume was then registered back to the CT volume. Registration was performed using Mattes mutual information method implemented in ITK 3.4[14]. This process was repeated 100 times using different random transformations. The result of registration is shown in FIG. 3.

The initial average error is the average distance between the correct position of the seeds (using the ground truth) and their perturbed positions. Registration error is the average distance between the correct position of the seeds and their position obtained from the registration. As it is shown in FIG. 3, the average registration error over 100 trials was 0.09 mm. Each registration took approximately three minutes on a Dell desktop computer running at 2.8 GHz with 3.5 GB of RAM. In order to examine the positive effect of phase congruency on registration, the same experiments as above were repeated, but without the phase congruency filter. Only noise reduction was performed on the ultrasound images. The average registration error jumped to 4.2 mm, clearly attesting to the positive effect of phase congruency.

In order to validate the robustness of our method to false positives in the US images, up to 15 seeds (about 30% of the total number of seeds) in the CT volume were randomly masked. For each percentage of false positives, registration was repeated 100 times by applying to the US data the same random transformations as in the earlier experiments. According to Table 3, registration remained robust up to 30% false positives, with maximum error of 0.52 mm.

The clinical requirement for registration is about 1.5 mm, which suggests that the method described herein will provide adequate performance in actual clinical cases. It is noted that clinical data does not contain apparent ground truth. Although explicit segmentation of the seeds from US images was not performed, a byproduct of this registration technique is, in fact, segmentation of seeds in the US images. In clinical cases, the accuracy of registration will be validated by comparing our automated seed segmentation to manual seed segmentation by multiple expert clinicians.

The calculation of phase congruency is the most computationally intensive step of the method. For each ultrasound image, this calculation currently takes about 13 seconds in MATLAB. Significant improvements in performance may be obtained by careful tuning of the parameters. For example, by recognizing the directionality of ultrasound images, the phase calculations at orientations near 90° may be removed without significantly affecting accuracy. Reducing the orientations to only 0°, 30° and 150° reduces the computation time by one-half and increases the registration error by only 0.09 mm.

TABLE 3

Registration error for up to 30% false positives (FP) in the data set.

| #of FP | FP % | Mean(Std) (mm) | Maximum Error(mm) | #of Failure |
|---|---|---|---|---|
| 1 | 2.4% | 0.08 (0.02) | 0.22 | 1 |
| 2 | 4.08% | 0.09 (0.01) | 0.22 | 1 |
| 3 | 6.12% | 0.11 (0.01) | 0.23 | 1 |
| 4 | 8.16% | 0.08 (0.02) | 0.22 | 0 |
| 5 | 10.29% | 0.09 (0.02) | 0.22 | 0 |
| 6 | 12.24% | 0.10 (0.02) | 0.22 | 0 |
| 7 | 14.28% | 0.11 (0.02) | 0.26 | 0 |
| 8 | 16.32% | 0.11 (0.02) | 0.24 | 0 |
| 9 | 18.36% | 0.16 (0.02) | 0.36 | 0 |
| 10 | 20.4% | 0.15 (0.03) | 0.38 | 0 |
| 11 | 22.44% | 0.14 (0.02) | 0.30 | 0 |
| 12 | 24.48% | 0.14 (0.02) | 0.31 | 0 |
| 13 | 26.53% | 0.18 (0.02) | 0.42 | 0 |
| 14 | 28.57% | 0.19 (0.02) | 0.44 | 0 |
| 15 | 30.67% | 0.22 (0.01) | 0.52 | 0 |

Example 3

Analysis of Effects of Edema in Prostate Brachytherapy

Despite strict control of the intra-operative workflow, during prostate brachytherapy, edema may occur and cause significant dosimetric uncertainties; an issue under intense clinical investigation. Next to faulty source placement, edema is the most significant cause of failure in localized prostate therapies [16]. If edematic fluid accumulates in the prostate, cancerous tissues receive proportionally less dosage and the cancer may eventually recur [17]. Edema may onset immediately after needle placement begins and continues to evolve during the procedure [18]. In a recent study, Tanaka et al. found that edema caused 30% average increase in prostate volume on the first day after implantation [19]. Edema typically subsides after 2-4 weeks with a half-life of 10 days [20]; however, by then much of the dose is already delivered due to the short half-life of the isotopes (Pd103=17 days, I125=60 days). The degree of edema varies from patient to patient with no apparent predictive factors for its magnitude or detrimental effects on implant dosimetry. In contemporary practice, patients are released from the operating room without analysis or quantitative measurement of seed positions and dosimetry, and the implant dosimetry is not evaluated until the post-operative CT.

Edema is considered as a major factor in the optimal timing of the post-implant CT [21]. Prior work only looked at edematic volume growth by contouring the prostate gland, but one has still not been able to tell whether an implant failed because of inadequate implantation, or because a perfectly executed implant was distorted by the ensuing edema. Currently there is no quantitative understanding of how the implant (i.e., location of implanted seeds) and the resulting dosimetry change between being completed in the operation and before being evaluated in post-operative CT. In absence of such quantitative data, it is difficult to determine the statistical nature of changes or any positive correlation between edema and the choice of seed locations relative to the internal prostate anatomy. In order to be able to approach these fundamental clinical questions, we map the intra-operative TRUS with post-operative CT and discern the dislocation of seeds and relevant anatomy. Seeds are well-tractable in CT due to their high contrast to the soft tissue background, but mapping post-implant CT to intra-operative TRUS is rather challenging. Large edematic tissue expansion, apparent seed migration, perturbations, anatomical deformation caused by changes in body position from lithotomy to supine, and changes of rectal pressure make registration difficult to achieve.

The method described in this example addresses the above-mentioned problems by tracking the motion of actual seeds, while prostate contouring remains available to characterize the shape and size of the organ.

3.1. Methods

Figure 4:
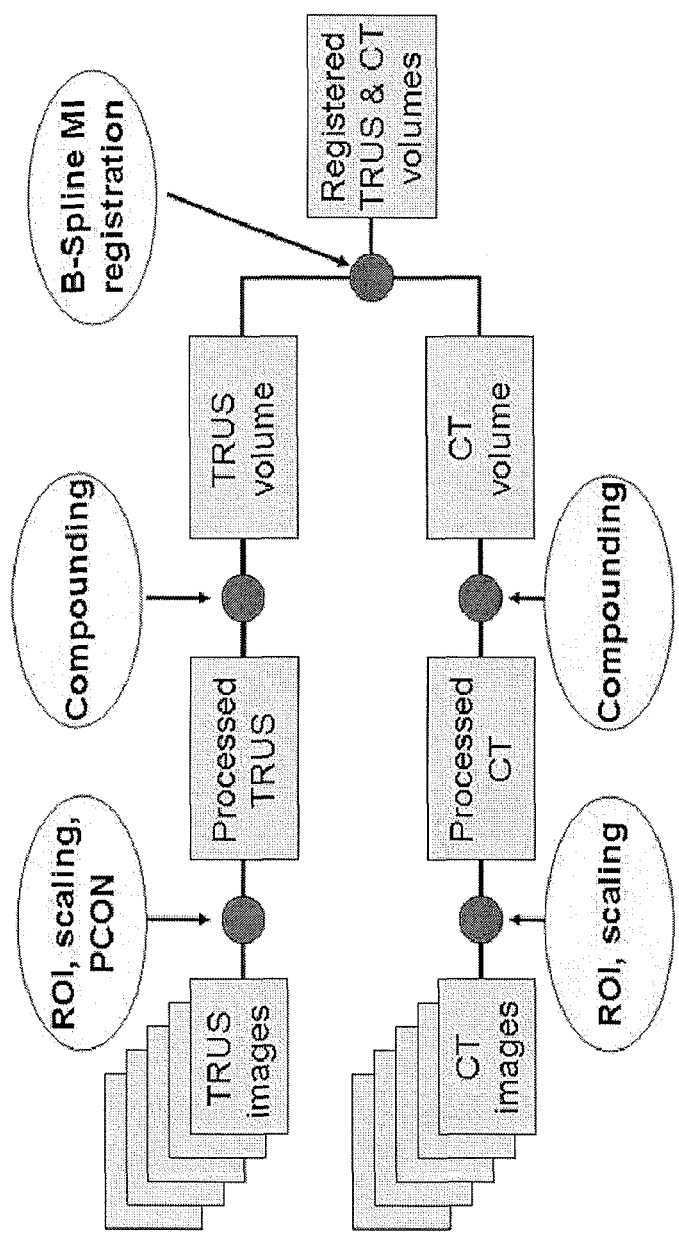
FIG. 4 is a block diagram showing the processing steps used in an embodiment used for quantifying the effect of edema on seed placement in brachytherapy.

TRUS is generally adequate for visualizing the prostate, but it suffers from many artifacts such as speckle, air-cavities, acoustic shadowing, reverberations, and multiple reflections. Because of this, in a fully implanted prostate, TRUS does not allow for robust and accurate localization of the implanted seeds. There have been recent efforts to register TRUS with intra-operative fluoroscopy for the purpose of in room dosimetry, in which case there is no deformation and seed motion. In these studies, seeds were segmented from both TRUS and fluoroscopy and registered with a variant of ICP [Su-2007] and network flow-based methods [4]. These segmentation-based methods are not sufficiently accurate and robust in a rigid and motionless case, so they cannot be expected to work in large tissue expansions and seed migration. Hence, an intensity-based registration procedure was used as shown in FIG. 4. The images were pre-processed with filters, the TRUS and CT volumes were compounded, and then B-spline deformable mutual information (MI) based multi-modal registration was applied. The objective in pre-filtering the volumes was to enhance seed-like regions without explicit segmentation of them. As seed-like regions are usually prominent in CT imaging, MI can lock on to these mutually pronounced regions.

Filtering:

In the CT volume, a region of interest was set around the prostate gland and simple window-level linear mapping was applied. In the TRUS volume, a region of interest was set around the gland, and the intensities were linearly scaled to the same range as the CT volume, in order to facilitate subsequent MI registration. The PCON technique discussed above was used to enhance features of true seeds by suppressing artifacts and false positives. PCON evaluates features based on phase rather than amplitude information. Since it gives a measure of significance for each point invariantly to image brightness or contrast, a constant and uniform threshold can be applied to extract feature points from the phase information [Kovesi-1999]. The PCON was calculated at each pixel of each image in order to measure the phase symmetry. The more symmetrical the phase of a region is, the more likely it is to be a seed. The measure of symmetry was calculated as the weighted average resulting from even and odd symmetry filters; because at symmetry points, the absolute values resulting from even and odd symmetry filters are large and small, respectively.

Registration:

B-spline deformable transformation was used with Mattes Mutual Information multi-modality 3D image-to-image metric. Edematic expansion offers itself to spline registration, where transformations interpolate control points extracted from both the source and target images to calculate the displacement required. Control points were selected using the mutual information similarity-based measure.

Ground Truth Phantom:

FIG. 2 shows the experimental ground truth phantom setup. The figure shows the relevant coordinate frames and transformations. These are not explained in detail here, since the process and notations are assumed to be familiar from basic surgical navigation literature. A realistic implant was made in a phantom (CIRS, Norfolk, Va.) 200 with 48 seeds 210 (12 are shown in the figure), a set of six 1 mm CT fiducials 220 was arranged on the container box, and a CT volume was acquired with 0.3 mm pixel size and 0.62 mm slice thickness. The seeds were carefully segmented from the CT and their locations converted to the coordinate frame defined by the fiducials, which were localized with a calibrated pointer (Traxtal Inc., Toronto, ON) 240 and Certus optical tracker (NDI, Waterloo, ON) 250. The TRUS probe 230 was calibrated [22], a series of tracked US images was collected from the phantom, and the images were computed to form a 3D volume. Finally, when the CT and TRUS volumes were registered, the seeds that had been segmented earlier from CT became known in the TRUS volume, providing accurate experimental ground truth data. In order to maximize tracking accuracy, the fiducials and tracking bodies were arranged so that their centroids fell close to the center of the prostate.

Edema Simulation:

Up to this point, the ground truth phantom data did not involve edematic expansion and seed motions. In lieu of expanding edema phantoms, these effects were produced computationally. Based on clinical literature, the edematic swelling was estimated with isotropic volume expansion [23]. This model is a fair one, since edema is caused by the physical trauma of the needle and seed insertions, and these are roughly uniformly distributed in the prostate volume. In actual implants, seed migrations and perturbations are superimposed on edematic swelling. Each seed travels with the swelling tissue and demonstrates its own motion and perturbation, seemingly independently from other seeds or the prostate itself. This effect was modelled with added random noise of variable amplitudes to the location and orientation of the seeds. The CT volume was therefore transformed as follows. Seeds had been segmented earlier and their centroids were known. For each seed, a small container box around the centroid was determined to fully include the seed. The seed boxes were digitally removed from the volume and the remaining intensities were smoothed with tri-linear interpolation. The seedless volume was expanded to simulate the edematic swelling. For each seed, the volume expansion transformation was applied to the centroid of the seed box. The seed boxes were not expanded, since the seeds themselves do not expand. To simulate seed motion and perturbation, translation and orientation noise was applied to each seed box via a transformation with tri-linear interpolation before the box was inserted back into the swollen volume. The amplitude of the swelling, and the location and direction noise were the variable parameters of the simulation. It is important to emphasize the edema model was applied in creating the ground truth test data and it has no bearing on the registration performance in actual human implant cases. Isotropic swelling, random migration, and random perturbation may be refined if needed, based on the statistical nature of the edema process.

3.2. Results and Discussion

To verify the reliability of the quantification methodology, different edema simulations were performed using four variables: prostate isotropic volumetric expansion, individual seed migrations, individual seed perturbation, and volume capture range. Five different datasets were generated with volumetric expansion from 0% to 45% percent, with 5% steps of the total prostate volume. For each dataset, a random translation was applied, with uniform distribution function, to each seed center of mass in the 'z' direction, i.e., approximate direction of the needle insertion paths. This is because random seed migration is not quite symmetrical in actual implants. Migration along the needle path tends to dominate and dislocations orthogonally to the needle path are almost negligible. The seed migration range was varied between ±1 mm and ±5 mm, with 1 mm steps. Random seed rotations were also applied between ±5 degrees and ±20 degrees. Volume transformations were applied between the ranges in ±5 mm translations and ±10 degrees rotations. Each random simulation was repeated 25 times to reach statistically significant results.

In actual brachytherapy procedures, initial pose estimation between TRUS and CT is very accurate and robust. The workflow is strictly controlled [18], allowing for precise determination of the directions of the main symmetry axes of the prostate. For CT imaging, the patient was positioned in supine pose with an empty rectum. For TRUS imaging, the patient was placed in lithotomy position with the TRUS probe in the rectum. This fact assures that with careful patient setup prostate rotations may be controlled about the lateral and AP axes very accurately, well within the capture range of the registration. The pitch angle of the prostate is also well-controlled by the setup, because for TRUS imaging the legs are held in stirrups of standard separation and elevation. The pitch angle of the prostate can be conveniently determined by fitting a standard ellipsoidal model on the midsection of the prostate capsule contoured in both TRUS and CT [24]. For all practical purposes, it is also safe to assume that false positives and missing seed appearances are approximately uniformly distributed in the CT and TRUS volumes. What follows is that after simple binary thresholding of the two volumes, the two gravity centers are practically identical. Jain et al. found this approach to be accurate to a few millimeters in intraoperative registration of C-arm fluoroscopy and TRUS of brachytherapy implants [2]. Thus, one may be confident that in actual clinical cases the initial pose will be conveniently determined, within a few millimeters and degrees, which will be well within the capture range.

ITK B-Spline deformable transformation was used with Mattes Mutual Information multi-modality 3D image-to-image metric to register the pre-processed TRUS and CT volumes. (The latter also underwent edema simulations, as described.) The Euclidean distance between each seed registration and the ground truth was measured. Since the method is essentially a correspondence algorithm, the percentage of correctly matched seeds, with mean error and STD, is the most informative metric to evaluate registration performance. The practical requirement for brachytherapy seed localization is about 2.0 mm (the diameter of the implant needle), which may be considered as the threshold for successful registration and matching between seeds.

According to Table 4, the registration pipeline produced 100% matching and correct registration for up to 40% volumetric isotropic expansion. The matching rate drops just slightly, to 98%, when a severe 45% expansion is applied. All the while, the mean registration error remains under 0.35 mm, which is an outstanding result from clinical perspective.

TABLE 4

Volumetric expansion.

| Volumetric Expansion (%) | Mean Registration Error in (mm) | SD (mm) | Successful Registrations |
|---|---|---|---|
| 10% | 0.08 | 0.05 | 100% |
| 20% | 0.30 | 0.08 | 100% |
| 30% | 0.19 | 0.12 | 100% |
| 40% | 0.22 | 0.33 | 100% |
| 45% | 0.35 | 0.82 | 98% |

Table 5 shows registration performance with uniform random seed orientation perturbation at a volume expansion of 10%. The average registration error remains well below the clinical threshold, while a 98% matching rate was obtained at ±10 degrees random rotation and 92% matching rate was obtained at ±20 degrees random rotation.

TABLE 5

Seed perturbation with 10% volumetric expansion.

| Seed Perturbation (degree) | Mean Registration Error in (mm) | SD (mm) | Successful Registrations |
|---|---|---|---|
| [−5, +5] | 1.30 | 0.59 | 98% |
| [−10, +10] | 1.53 | 0.24 | 98% |
| [−15, +15] | 1.02 | 0.38 | 92% |
| [−20, +20] | 1.34 | 0.49 | 92% |

Table 6 shows registration performance with uniform random seed migration at a volume expansion of 10%. The average registration error holds up well below the clinical threshold, while a 95% matching rate was obtained at ±3 mm random migration and a 90% matching rate was obtained at ±5 mm random migration.

To test capture range, registrations were run at a severe 45% volume expansion and ±5 mm random migration, with random translation and angular misalignments of ±5 mm and ±10 degrees, respectively. To gain statistical significance, 25 random cases were run. With the initial misalignment, the method achieved 95% successful registrations with volume expansion and 90% with random seed migrations while the mean registration error and SD were within the clinically acceptable range.

TABLE 6

Seed migration with 10% volumetric expansion.

| Seed Migration (mm) | Mean Registration Error in (mm) | SD (mm) | Successful Registrations |
|---|---|---|---|
| [−1, +1] | 1.20 | 0.39 | 100% |
| [−2, +2] | 1.23 | 0.40 | 98% |
| [−3, +3] | 1.42 | 0.39 | 95% |
| [−4, +4] | 1.38 | 0.43 | 95% |
| [−5, +5] | 1.60 | 0.38 | 90% |

It is noted that the primary endpoint of this edema characterization embodiment is not dosimetry. The main objective is to understand statistical correlations between needle paths and edematic swelling and between implanted seed locations and seed migrations. Hence mismatched seeds were omitted from the statistics. In other words, as long as the registration error of correctly matched seeds remains low and the matching percentage remains reasonably high, "renegade seeds" are not considered. Renegade seeds are seeds that migrate severely, sometimes up to 10 mm or more, in ducts, needle tracts and blood vessels. With this in mind, the BSDR analysis performs well. However, it is expected that other techniques, including alternative MI techniques, may suitably allow for local deformations, such as the ones caused by larger seed migrations.

Edema characterization is among the few interventional imaging problems where calculation speed is not critical, because the analysis takes place postoperatively. Pre-filtering the full TRUS volume took 13.0 sec in MATLAB. The ITK/C++ implementation of the B-spline deformable MI-based registration ran approximately 201.0 sec, using an Intel Duo processor with a 1.66 GHz CPU and 2 GB RAM. Our software was not optimized for speed or memory efficiency.

Example 4

Point-to-Volume Registration of Ultrasound to Fluoroscopy

As an alternative to volume-to-volume registration, the following is an example of a point-to-volume technique that maps a 3D point cloud to a moving volume. As with volume-to-volume registration, the goal is to determine the set of parameters of the transformation that optimizes a specified metric. In this example, point-to-volume intensity-based registration is presented in a clinical context of localizing prostate brachytherapy seeds. Presented are an implementation and detailed experimental analysis on a ground truth phantom and initial results on patient data.

4.1 Method

Phantom data were obtained using the experimental ground truth phantom setup described in section 1.4 of Example 1, above, and shown in FIG. 2. Tracked TRUS acquisition was used to scan the phantom systematically with translational motion and continuous image capture. The in-plane pixel size was 0.14×0.13 mm$^2$. Inter-frame spacing was about 0.5 mm. Following filtering, an 8-bit image volume was compounded from the 2D slices. As described above, the positions of seeds segmented in CT images were transformed to the TRUS coordinate system, thereby defining the ground truth (see FIG. 2) for the registration.

Clinical patient data were obtained from C-arm fluoroscopy images of patients at Johns Hopkins Hospital in Baltimore, Md., U.S.A., under ethics board approval.

Registration Algorithm:

We assumed a coordinate system of the fixed 3D point cloud (CT/Fluoroscopy) as a reference and searched for a transform that mapped points from the space of the fixed point set to the space of the moving image. The fixed point set coordinates were assigned intensity values as well and since a binarized point cloud was considered, an intensity value of 255 (i.e., sample coordinate (X,Y,Z,255) was automatically assigned. Two metrics were tested for this technique: the Normalized Correlation (NC) and Mean Squares metrics (MS) [25]. Clinically, there is always an accurate and consistent initial guess for the registration. Standard patient positioning allows for estimating the main symmetry axes of the prostate, and alignment of the gravity centers of the TRUS volume and the seed cloud yields an accurate guess for translation [2]. The "one plus one evolution strategy", denoted by (1+1)-ES, was used for algorithm optimization and parameter convergence.

4.2 Results

Phantom Results:

For the point-to-volume registration technique, results for the NC metric were less accurate when compared to the above volume-to-volume analysis (see Example 1). As seen in Table 7, filtering the TRUS data was beneficial, as 6 of the 7 filters (discussed in Example 1) yielded more precise TRE values than the unfiltered TRUS. In particular, US6 filter showed the best value of 0.54±1.36 mm. The MS metric showed stronger statistical significance for average and standard deviation. Still, all filters yielded a final TRE below 1.0 mm. In the false positive analyses the MS metric yielded excellent TRE below 2 mm. The least accurate filter was achieved with the US3 (TRE of 0.87±0.11 mm). With the NC metric, results deteriorated as the least precise value was again achieved with the US3 filter yielding (TRE of 1.97±1.34 mm) for the false positive analysis. The un-optimized MATLAB code for P2V executed in 90 seconds, in average, on an Intel Core2, 2.4 GHz dual-core computer.

TABLE 7

Mean and standard deviation of TRE in phantom trials for point-to-volume registration (all units in mm)

| Filter | Target Registration Error (TRE) | |
|---|---|---|
| | NC | MS |
| US0 | 1.19 ± 1.99 | 0.40 ± 0.17 |
| US1 | 0.58 ± 1.44 | 0.70 ± 0.22 |
| US2 | 0.88 ± 1.68 | 0.49 ± 0.12 |
| US3 | 1.89 ± 2.23 | 0.56 ± 0.12 |
| US4 | 0.67 ± 1.67 | 0.38 ± 0.19 |
| US5 | 0.66 ± 1.75 | 0.65 ± 0.24 |
| US6 | 0.54 ± 1.36 | 0.88 ± 0.17 |
| US7 | 0.76 ± 1.51 | 0.83 ± 0.21 |

Clinic Results:

Seeds were reconstructed from four C-arm fluoroscopy images as a cloud of seeds using the method of Jain et al. [26], compounded into a binary CT volume. Point-to-volume registration was performed with both NC and MS metrics. A visual inspection of the resulting images revealed that there was no fluoroscopy seed without a corresponding white blotch in TRUS, suggesting that there were no false negatives. As expected, there were some white blotches in TRUS without corresponding seeds from fluoroscopy, suggesting the presence of false positives. At the same time, the expert clinician had difficulty in segmenting the dense series of TRUS slices with many seeds extending across consecutive images. For one patient, C-arm fluoroscopy reconstructed all the 81 implanted seeds. In the TRUS data, the expert clinician identified only 41 seeds with confidence, while 40 seeds could not be distinguished from noise and artifacts. Based on the 41 seeds positively segmented in TRUS, the average TRE was 2.86 mm, with a standard deviation of 1.26 mm.

4.3 Discussion

Evaluation of the point-to-volume intensity-based registration technique on data collected from a prostate phantom implanted with 48 dummy seeds indicated that TRE was consistently below clinical threshold (<2 mm), capture range was significantly larger than the initial guess guaranteed by the clinical workflow, robustness was excellent to false positive seed appearances, and temporal performance was acceptable. Initial results on clinical data confirmed the utility f the technique.

The contents of all references, pending patent applications, and published patents cited throughout this application are hereby expressly incorporated by reference.

EQUIVALENTS

Those skilled in the art will recognize or be able to ascertain variants of the embodiments described herein. Such variants are within the scope of the invention and are covered by the appended claims.

REFERENCES

1. Jemal A, et al. Cancer statistics, 2007. *CA Cancer J Clin.,* 57(1):43-66 (2007).
2. Jain A K, et al. Intra-operative Guidance in Prostate Brachytherapy Using an Average C-arm. In: Ayache N, et al. (eds.) *Medical Image Computing and Computer-Assisted Intervention,* MICCAI-2007, Part II LNCS 4792, pp 9-16, Springer, Heidelberg.
3. Su Y, Davis B J, Furutani K M, Herman M G, Robb R A. "Seed localization and TRUS-fluoroscopy fusion for intra-operative prostate brachytherapy dosimetry," *Computer Aided Surgery,* 12(1):25-34 (2007).
4. Tutar I B, Narayanan S, Lenz H, Nurani R, Orio P, Cho P S, Wallner K, Kim Y. "Seed-based ultrasound and fluoroscopy registration using iterative optimal assignment for intraoperative prostate brachytherapy dosimetry," *SPIE Medical Imaging,* pp. 65091-650914 (2004).
5. Liu X, Jain A K, Fichtinger G. Prostate Implant Reconstruction with Discrete Tomography, *Medical Image Computing and Computer-Assisted Intervention,* LNCS 4791, pp 734-741 (2007).
6. Kaplan I D, et al. Real-time computed tomography dosimetry during ultrasound-guided brachytherapy for prostate cancer, *Brachytherapy,* 5(3):147-51 (2006).
7. Létourneau, D, Wong J W, Oldham M, et al., Cone-beam-CT guided radiation therapy: technical implementation, *Radiother Oncol,* 75(3):279-86 (2005).
8. Zhang M, Zaider M, Worman M F, Cohen G N. "On the question of 3D seed reconstruction in prostate brachytherapy: the determination of x-ray source and film locations," *Phys. Med. Biol.,* 49:335-345 (2004).
9. Gong L, Cho P S, Han B H, Wallner K E, Sutlief S G, Pathak S D, Haynor D R, Kim Y. "Ultrasonography and fluoroscopic fusion for prostate brachytherapy dosimetry," *Intl. J. Radiation Biol. Phys.,* 54:1322-1330 (2002).
10. Hacihaliloglu I, Abugharbieh R, Hodgson A J, Rohling R N. "Enhancement of bone surface visualization from 3D ultrasound based on local phase information," *IEEE Ultrasonics Symp.,* pp 21-24 (2006).
11. Kovesi P. "Image feature from phase congruency," *Vider: A Journal of Computer Vision Research,* MIT press, 1(3): 1-27 (1999).

12. Chen T K, Abolmaesumi P, Thurston A D, Ellis R E. "Automated 3D freehand ultrasound calibration with real-time accuracy control," *Medical Image Computing and Computer-Assisted Intervention*, pp 899-906 (2006).
13. Scepanovic D, Krishtein J, Jain A K, Taylor R H. "Fast Algorithm for Probabilistic Bone Edge Detection (FAPBED)," *SPIE Medical Imaging: Image Processing* (2005).
14. Mattes D, Haynor D R, Vesselle H, Lewellen T K, Eubank W. "PET-C T image registration in the chest using free-form deformations," *IEEE Trans. Medical Imaging*, 22(1): 120-128 (2003).
15. Gobbi D G, Peters T M. "Newblock interactive intraoperative 3D ultrasound reconstruction and visualization," *Medical Image Computing and Computer-Assisted Intervention*, LNCS 2489, pp 156-163 (2002).
16. Yamada Y, et al. Impact of intraoperative edema during transperineal permanent prostate brachytherapy on computer-optimized and preimplant planning techniques. *Am. J. Clin. Oncol.* 26(5):130-135 (2003).
17. Roberson P L, et al. Source placement error for permanent implant of the prostate. *Med. Phys.* 24:251-257 (1997).
18. Wallner K, et al. Prostate brachytherapy made complicated, 2nd edn. Smart Medicine Press, Seattle (Wash.) (2001).
19. Tanaka O, et al. Effect of edema on postimplant dosimetry in prostate brachytherapy using CT/MRI fusion. *Int. J. Radiat. Oncol. Biol. Phys.* 69:614-618 (2007).
20. Waterman F M, et al. Edema associated with 1-125 or Pd-103 prostate brachytherapy and its impact on post-implant dosimetry: An analysis based on serial CT acquisition. *Int. J. Radiat. Oncol. Biol. Phys.* 41:1069-1077 (1998).
21. Prestidge A R, et al.: Timing of computed tomography-based postimplant assessment following permanent transperineal prostate brachytherapy. *Int. J. Radiat. Oncol. Biol. Phys.* 40:1111-1115 (1998).
22. Mercier L, et al. A review of calibration techniques for freehand 3-D ultrasound systems. *Ultrasound Med. Biol.* 31(4):449-471 (2005).
23. Kim Y, et al. Dosimetric Impact of Prostate Volume Change Between CT-Based HDR Brachytherapy Fractions. *Int. J. Radiat. Oncol. Biol. Phys.* 59(4):1208-1216 (2004).
24. Amink R, et al. Planimetric volumetry of the prostate: how accurate is it? *Physiol. Meas.* 16:141-150 (1995).
25. Yoo, T. S., Ackerman M. J., Lorensen W. E., et al., "Engineering and Algorithm Design for an Image Processing API: A Technical Report on ITK—The Insight Toolkit," Proc. of Medicine Meets Virtual Reality, 85, 586-592 (2002).
26. Jain, A. K., Deguet, A., Iordachita, I., et al., "Intra-operative 3D guidance in prostate brachytherapy using an average c-arm," Medical Image Computing and Computer-Assisted Intervention, 4792, 9-17 (2007).
27. Mattes D., Haynor D. R., Vesselle H., Lewellen T. and Eubank W. Nonrigid multimodality image registration. *Proc. SPIE Medical Imaging: pp.* 1609-1620, 2001.

The invention claimed is:

1. A method for combining ultrasound image data and X-ray, MRI, or pre-implant plan image data of a material containing a plurality of markers, comprising using a computer to perform processing steps including:
   processing ultrasound, X-ray, or MRI image data and constructing a first volume from the image data, the first volume including data corresponding to at least a portion of the markers;
   processing X-ray image data, MRI image data, or pre-implant plan image data and constructing a second volume or a three dimensional (3D) point set from the image data, the second volume or 3D point set including data corresponding to at least a portion of the markers;
   constructing a combined image by applying 3D intensity-based registration, or a derivative thereof, to align data corresponding to the markers in the first and second volumes or the first volume and the 3D point set; and
   outputting the combined image comprising the ultrasound image data and the X-ray, MRI, or pre-implant plan image data of the material containing a plurality of markers.

2. The method of claim 1, wherein processing ultrasound image data comprises filtering the image data using an analysis with respect to space or frequency, and processing X-ray image data or MRI image data comprises filtering the data using an analysis with respect to space or frequency.

3. The method of claim 2, wherein filtering the ultrasound image data includes applying at least one of a statistical analysis, a stochastic analysis, a fractal analysis, a wavelet analysis, a spectral analysis, a beam profile analysis, and array processing, and filtering the X-ray image data or MRI image data includes applying at least one of a statistical analysis, a stochastic analysis, a fractal analysis, a wavelet analysis, a spectral analysis, and array processing.

4. The method of claim 2, wherein filtering the image data includes applying to each of said ultrasound image data, X-ray image data, or MRI image data at least one of window-level scaling, binary thresholding, noise reduction filtering, thresholding, averaging, median filtering, speckle reduction, diffusion filtering, anisotropic filtering, phase congruency, phase symmetry, gradient filtering, and contrast enhancement filtering.

5. The method of claim 1, wherein processing ultrasound image data and/or processing X-ray or MRI image data includes filtering only a region of interest selected from the ultrasound image data and/or the X-ray or MRI image data.

6. The method of claim 1, wherein processing pre-implant plan image data comprises applying an imaging-blurring filter.

7. The method of claim 1, wherein the image data are associated with a medical intervention.

8. The method of claim 1, wherein the markers are selected from radioactive seeds and surgical clips.

9. The method of claim 7, wherein the image data are associated with a brachytherapy procedure.

10. The method of claim 9, wherein the brachytherapy procedure is associated with treating prostate cancer.

11. A method for combining ultrasound image data and X-ray, MRI, or pre-implant plan image data of a material containing a plurality of markers, comprising using a computer to perform processing steps including:
   project one of an ultrasound, X-ray, MRI, or pre-implant plan volume on one other of an ultrasound, X-ray, MRI, or pre-implant plan volume to generate at least one first 2D projection, the first projection including at least a portion of the markers;
   process X-ray image data, or project X-ray image data, MRI image data, or pre-implant plan image data to generate at least one second 2D projection, the processed X-ray image data or the second projection including at least a portion of the markers;
   apply 2D intensity-based registration, or a derivative thereof, to align the markers in the first 2D projection and the processed X-ray image data; or to align the first and second 2D projections; and output a combined image comprising the ultrasound image data and X-ray, MRI, or pre-implant plan image data of the material containing a plurality of markers.

12. The method of claim 11, wherein projecting ultrasound image data comprises filtering the image data using an analysis with respect to space or frequency, and processing X-ray image data or projecting X-ray or MRI image data comprises filtering the image data using an analysis with respect to space or frequency.

13. The method of claim 11, wherein filtering the ultrasound image data includes applying at least one of a statistical analysis, a stochastic analysis, a fractal analysis, a wavelet analysis, a spectral analysis, a beam profile analysis, and array processing, and filtering the X-ray or MRI image data includes applying at least one of a statistical analysis, a stochastic analysis, a fractal analysis, a wavelet analysis, a spectral analysis, and array processing.

14. The method of claim 13, wherein filtering the image data includes applying to each of said ultrasound image data, X-ray image data, or MRI image data at least one of window-level scaling, binary thresholding, noise reduction filtering, thresholding, averaging, median filtering, speckle reduction, diffusion filtering, anisotropic filtering, phase congruency, phase symmetry, gradient filtering, and contrast enhancement filtering.

15. The method of claim 11, wherein projecting ultrasound image data and/or processing X-ray image data or projecting X-ray or MRI image data includes filtering only a region of interest selected from the ultrasound image data and/or the X-ray or MRI image data.

16. The method of claim 11, wherein projecting pre-implant plan image data comprises applying an imaging-blurring filter.

17. The method of claim 11, wherein the image data are associated with a medical intervention.

18. The method of claim 11, wherein the markers are selected from radioactive seeds and surgical clips.

19. The method of claim 17, wherein the image data are associated with a brachytherapy procedure.

20. The method of claim 19, wherein the brachytherapy procedure is associated with treating prostate cancer.

21. The method of claim 1, further comprising:
assessing marker placement in the material based on the combined image.

22. The method of claim 21, wherein the markers are radioactive seeds in a medical intervention and the material is a patient's anatomy.

23. The method of claim 22, wherein the medical intervention is a brachytherapy procedure.

24. The method of claim 11, further comprising:
assessing marker placement in the material based on the combined image.

25. The method of claim 24, wherein the markers are radioactive seeds in a medical intervention and the material is a patient's anatomy.

26. The method of claim 25, wherein the medical intervention is a brachytherapy procedure.

27. Programmed media for use with a computer and with ultrasound image data and X-ray, MRI, or pre-implant plan image data, the image data pertaining to a material having a plurality of markers, the programmed media comprising:
a computer program stored on non-transitory storage media compatible with the computer, the computer program containing instructions to direct the computer to perform one or more of:
process ultrasound image data to construct a first volume, the first volume including data corresponding to at least a portion of the markers;
process X-ray image data, MRI image data, or pre-implant plan image data to construct a second volume or to construct a three dimensional (3D) point set, the second volume or 3D point set including data corresponding to at least a portion of the markers;
apply 3D intensity-based registration, or a derivative thereof, to align data corresponding to the markers in the first and second volumes or the first volume and the 3D point set, to produce a combined image; and
output the combined image including markers.

28. Programmed media for use with a computer and with ultrasound image data and X-ray, MRI, or pre-implant plan image data, the image data pertaining to a material having a plurality of markers, the programmed media comprising:
a computer program stored on non-transitory storage media compatible with the computer, the computer program containing instructions to direct the computer to perform one or more of:
project an ultrasound volume to generate at least one first 2D projection, the first projection including at least a portion of the markers;
process X-ray image data, or project X-ray image data, MRI image data, or pre-implant plan image data to generate at least one second 2D projection, the processed X-ray image or the second projection including at least a portion of the markers;
apply 2D intensity-based registration, or a derivative thereof, to align the markers in the first 2D projection and the processed X-ray image data; or to align the first and second 2D projections, to produce a combined image; and
output the combined image including markers.

29. A system for generating an output image from ultrasound image data of a material and X-ray, MRI, or pre-implant plan image data of the material, the material having a plurality of markers, the system comprising:
a computer;
the programmed media of claim 27; and
hardware associated with one or more imaging modalities;
wherein the output image includes markers.

30. A system for generating an output image from ultrasound image data of a material and X-ray, MRI, or pre-implant plan image data of the material, the material having a plurality of markers, the system comprising:
a computer;
the programmed media of claim 28; and
hardware associated with one or more imaging modalities;
wherein the output image includes markers.

* * * * *